United States Patent [19]
Kilburn et al.

[11] Patent Number: 5,928,917
[45] Date of Patent: Jul. 27, 1999

[54] CONJUGATE OF NON-PROTEIN CHEMICAL MOIETY AND POLYPEPTIDE HAVING CELLULOSE BINDING REGION

[75] Inventors: Douglas G. Kilburn, Vancouver; Robert C. Miller, North Vancouver; Neil Gilkes; R. Antony J. Warren, both of Vancouver, all of Canada

[73] Assignee: University of British Columbia, Canada

[21] Appl. No.: 08/249,037

[22] Filed: May 24, 1994

Related U.S. Application Data

[63] Continuation of application No. 07/865,095, Apr. 8, 1992, Pat. No. 5,340,731, which is a continuation-in-part of application No. 07/603,987, Oct. 25, 1990, Pat. No. 5,202,247, which is a division of application No. 07/216,794, Jul. 8, 1988, Pat. No. 5,137,819.

[51] Int. Cl.$^6$ .......................... C12N 11/12; C12N 15/00; C12P 21/00

[52] U.S. Cl. .............................. 435/179; 435/4; 435/69.1; 435/69.52; 435/69.7; 435/71.1; 435/172.3; 435/177; 435/195; 435/200; 435/209; 435/803; 436/530; 530/402; 530/808; 530/814; 935/11; 935/14

[58] Field of Search .......................... 435/4, 69.1, 69.52, 435/69.7, 71.1, 172.3, 177, 179, 195, 200, 209, 803; 436/530; 530/402, 808, 814; 935/11, 14

[56] References Cited

U.S. PATENT DOCUMENTS

| | | | |
|---|---|---|---|
| 4,745,055 | 5/1988 | Schenk et al. | 435/172.3 X |
| 5,137,819 | 8/1992 | Kilburn et al. | 435/179 |
| 5,202,247 | 4/1993 | Kilburn et al. | 435/195 |
| 5,340,731 | 8/1994 | Kilburn et al. | 435/179 |
| 5,643,758 | 7/1997 | Guam et al. | 435/69.7 |

FOREIGN PATENT DOCUMENTS

| | | |
|---|---|---|
| 0244147A2 | 4/1987 | European Pat. Off. . |
| 0286239A1 | 3/1988 | European Pat. Off. . |
| 0195680 | 9/1996 | European Pat. Off. . |
| WO 94/24158 | 10/1994 | WIPO . |

OTHER PUBLICATIONS

Bedouelle & Duplay, *Eur. J. Biochem.* (1988) 171:541–549.
Boyer et al., *Biotechnology & Bioengineering* (1987) 29:176–179.
Ghose & Bisaria, *Biotechnology & Bioengineering* (1979) 21:131–146.
Gilkes et al., *Bio/Technology* (1984) 2:259–263.
Gilkes et al., *J. Biol. Chem.* (1984) 259:10455–10459.
Gilkes et al., *J. Microbiol.* (1984) 130:1377–1384.
Gilkes et al., *J. Biol. Chem.* (1988) 263:10401–10407.
Greenburg et al., *J. Bacteriol.* (1987) 169:4574–4677.
Greenwood et al., *FEBS Letters* (1989) 244:127–131.
Gutierrez et al., *J. Mol. Biol.* (1987) 195:289–297.
Halliwell & Griffin, *Biochem. J.* (1978) 169:713–715.
Kellett et al., *Biochem. J.* (1990) 272:369–376.
Langsford et al., *J. General Microbiol.* (1984) 130:1367–1376.
Langsford et al., *FEBS Letters* (1987) 225:163–167.
Moloney & Coughlan, *Biotechnology & Bioengineering* (1983) 25:271–280.
Moser et al., *Applied & Environmental Microbiol.* (1989) 55:2480–2487.
Nummi et al., *Analytical Biochemistry* (1981) 116:137–141.
O'Neill et al., *Gene* (1986) 44:325–330.
Ong et al., *Bio/Technology* (1989) 7:604–607.
Ooshima et al., *Biotechnology & Bioengineering* (1983) 25:3103–3114.
Remaut et al., *Gene* (1983) 22:103–113.
Ryu et al., *Biotechnology & Bioengineering* (1984) 26:488–496.
"Sequence Homology Between Putative Raw–Starch Binding Domains" *Biochem. J.* (1989) 264:309–311.
Svensson et al., *Eur. J. Biochem.* (1986) 154:497–502.
Takahashi et al., *J. Biochem.* (1985) 98:663–671.
Teeri et al., *Gene* (1987) 51:43–52.
Tomme et al., *Eur. J. Biochem.* (1988) 170:575–581.
Van Tilbeurgh et al., *FEBS Letters* (1986) 204:223–227.
Vieira & Messing, *Gene* (1982) 19:259–268.
Warren et al., *Proteins: Structure, Function & Genetics* (1986) 1:335–341.
Warren et al., *Gene* (1987) 61:421–427.
Watanabe et al., *J. Bacteriol.* (1980) 172:4017–4022.
Watanabe et al., *J. Biol. Chem.* (1990) 265:15659–15665.
Whittle et al., *Gene* (1982) 17:139–145.
Williamson & Stutzenberger, *Letters in Applied Microbiology* (1987) 5:101–105.
Wong et al., *Gene* (1986) 44:315–324.
Yanisch–Perron et al., *Gene* (1985) 33:103–119.
Zoller & Smith, *Nucl. Acids Res.* (1982) 10:6487–6501.
Zoller & Smith, *Methods in Enzymology* (1983) 100:468–501.
Owolabi et. al., Applied and Environmental Microbiology, vol. 54, No. 2, Feb. 1988, pp. 518–523.

*Primary Examiner*—David M. Naff
*Attorney, Agent, or Firm*—Rae-Venter Law Group, P.C.

[57] ABSTRACT

Fusion proteins or conjugates are provided containing an amino acid sequence having a substrate binding region of a polysaccharidase such as cellulase that binds to a β-1,4-glycan matrix such as cellulose. The substrate binding region is essentially without polysaccharidase activity. In the fusion protein, the substrate binding region is fused or chemically linked to a polypeptide such as an enzyme, a hormone, an immunoglobulin or a protein dye. By contacting the fusion protein with a β-1,4-glycan matrix, the substrate binding region binds to the matrix to immobilize the polypeptide on the matrix. The polypeptide or fusion protein can be removed from the matrix with a protease recognition sequence or with a solution having a low ionic strength or high pH. In the conjugate, the substrate binding region is joined such as by covalent bonding to a non-protein chemical moiety such as a dye, chromophore, fluorescor, radionuclide or enzyme co-factor. By contacting the conjugate with a β-1,4-glycan matrix, the substrate binding region binds to the matrix to immobilize the chemical moiety on the matrix. The conjugate or chemical moiety can be removed with a protease acting on a protease recognition sequence or with a solution having a low ionic strength or high pH.

43 Claims, 20 Drawing Sheets

FIG. 1

| Plasmid | Promoter | R.B.S. | Sequence of the Exg or Exg-BGal fusion | Exg activity[3] |
|---|---|---|---|---|
| pUC12-1.1cex | lac | cex | AGGAGGACATC ... -41 -39 -37 -35 -3 -2 -1 +1 +2<br>M P R T T P A A Q A A T<br>ATGCCTAGGACCACGCCCCGCA...GCCCAGGCCGCGACC......1.0 | 1.0 |
| pUC12-1.1(737) | lac | lacZ | AGGAAACAGCT T M I T N S s s P g d P R<br>ATGACCATGATTACGAATTCGAGCTCGCCCGGGATCCTAGG....150<br>BamHI StyI | 150 |
| pUC12-1.1(PTIS) | lac | PTIS | TGGAGGAAAAATT (-40)<br>M D P R I<br>ATGGATCCTAGGACC........<br>BamHI StyI | 146 |

FIG. 3

S=SalI; B=Bam HI;Ec=Eco RI; ▦=MULTIPLE CLONING SITE; ▨=PT BOX; X=Xma III; ▥=~ 8 KDa BINDING REGION; ☐ =C. fimi DNA; NUMBER IN PARENTHESIS IS THE SIZE OF THE CODING SEQUENCE; ALL OTHER NUMBERS REFER TO INSERT NUCLEOTIDE NUMBER; ▨ = PTIS,

◨ = AVICEL ALONE; ▨ = MEDIUM + CELLS;
▦ = AVICEL + SBD-β GLUCOSIDASE.

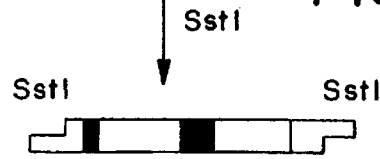
FIG. 10A
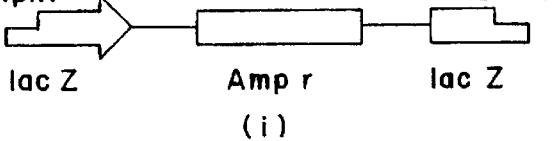
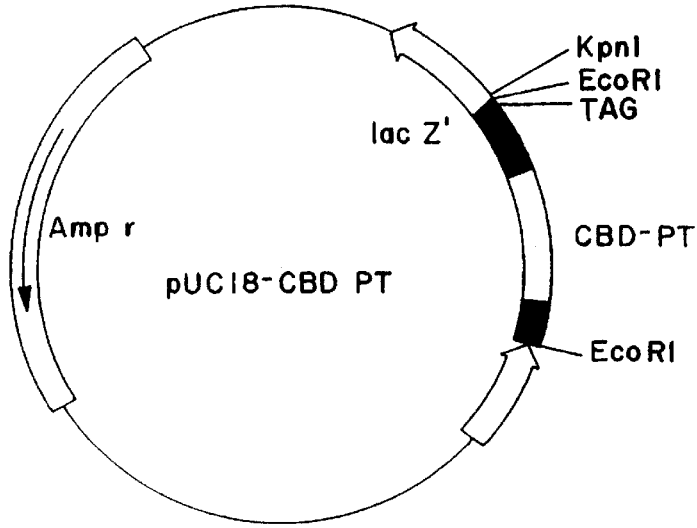
FIG. 10B
```
1                    32                           164
M  S    T  A  A  Q  A  A  P  G  C    T  P  T  P  •
ATG TCC...ACC GCC GCG CAG GCG GCT CCC GGC TGC.....ACC CCC ACG CCG TAG
```
FIG. 10C

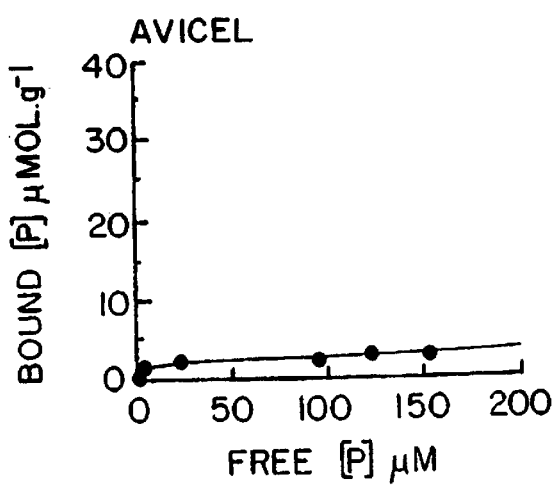
FIG. 15A
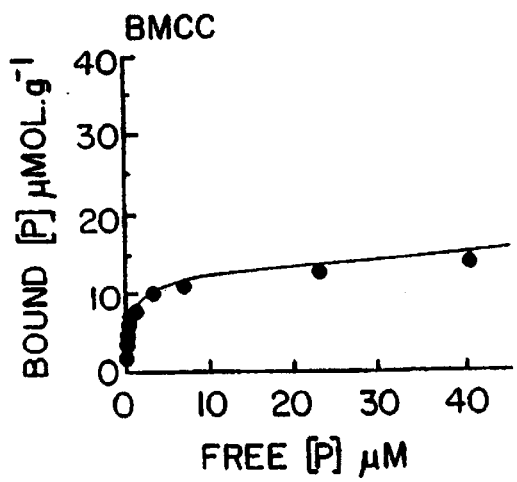
FIG. 15B
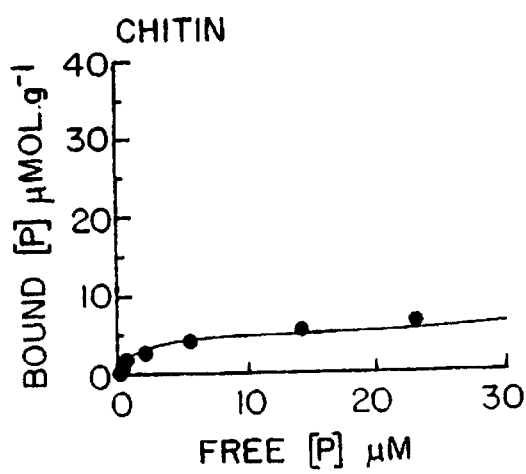
FIG. 15C
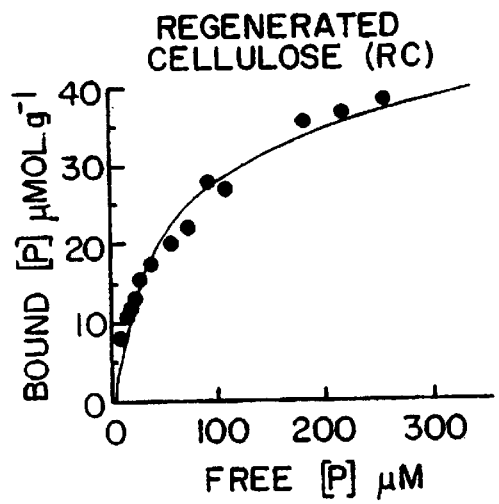
FIG. 15D
| SUBSTRATE | SATURATION LEVEL ($\mu MOL.g^{-1}$) |
|---|---|
| AVICEL | >3 |
| BMCC | >15 |
| CHITIN | >7 |
| RC | >40 |
FIG. 15E

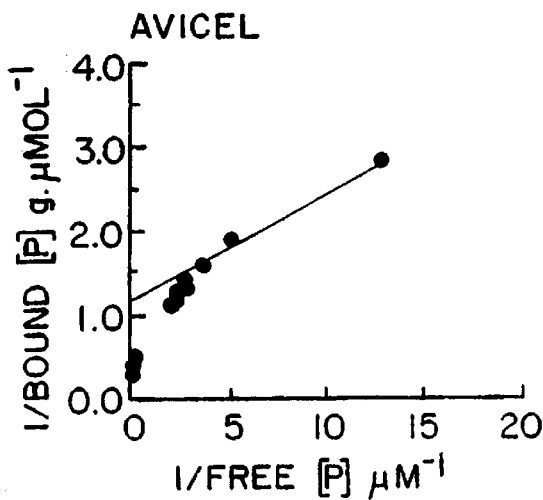
FIG. 16A
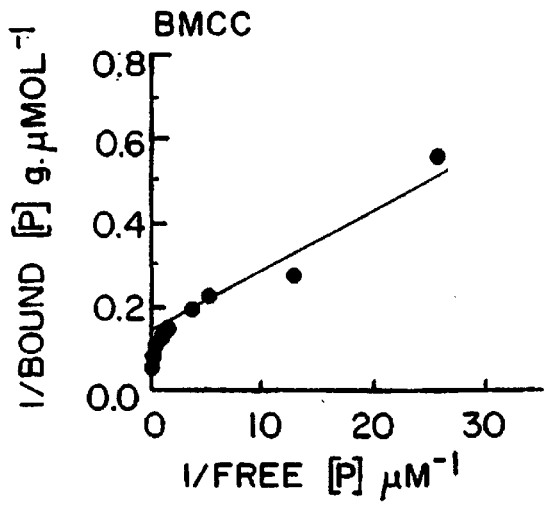
FIG. 16B
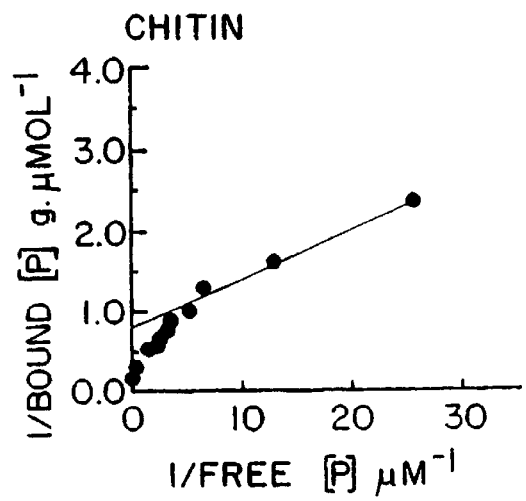
FIG. 16C
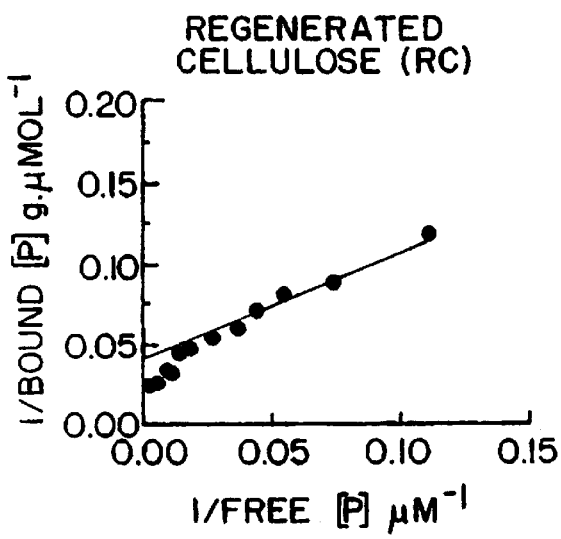
FIG. 16D
| SUBSTRATE | RELATIVE AFFINITY (L.g$^{-1}$) |
|---|---|
| AVICEL | 8 |
| BMCC | 58 |
| CHITIN | 18 |
| RC | 1 |
FIG. 16E 1 2 3 4 5 6 7 8 9 10

1 2 3 4 5 6 7 8 9 10

CONJUGATE OF NON-PROTEIN CHEMICAL MOIETY AND POLYPEPTIDE HAVING CELLULOSE BINDING REGION

This application is a continuation of U.S. patent application Ser. No. 07/865,095, filed Apr. 8, 1992 and now issued as U.S. Pat. No. 5,340,731, which is a continuation-in-part of U.S. patent application Ser. No. 07/603,987, filed Oct. 25, 1990 and now issued as U.S. Pat. No. 5,202,247, which is a divisional of U.S. patent application Ser. No. 07/216,794, filed Jul. 8, 1988 and now issued as U.S. Pat. No. 5,137,819, which enclosures are incorporated herein by reference.

INTRODUCTION

1. Technical Field

This invention relates to novel removable labels comprising chimeric polypeptides and polypeptide conjugate-chemical moiety conjugates which are capable of binding to a polysaccharide matrix, and methods for their preparation and use.

2. Background

Production of foreign proteins by expression in microbial systems can become a significant source of high value, medically important proteins. Purification and recovery of recombinant proteins are major considerations in the design of a fermentation process. While traditional means of protein purification can be used to isolate a product, improved means include the use of fusion proteins. Fusion proteins can be purified by affinity chromatography, the desired component of the fusion protein being purified by virtue of its covalent attachment to a polypeptide which binds to an affinity matrix. As an example, fusion proteins comprising a polypeptide of interest fused to β-galactosidase can be purified using a p-amino-phenyl-β-D-thiogalactoside-Sepharose column. Such a method has been used for purification of immunogenic polypeptides such as viral antigens. Staphylococcal protein A can also be used for affinity purification of fusion proteins by virtue of its specific binding to the Fc portion of immunoglobulins.

In addition to purification, recovery of the original components from the fusion is often desirable. Both chemical and biological methods have been devised to cleave fusion proteins into their component polypeptides or segments. Introduction of acid-labile aspartyl-proline linkage between the two segments of a fusion protein facilitates their separation at low pH. The major requirement of this system is that the desired segment of interest is not acid-labile. Fusion proteins comprising hormones such as insulin and somatostatin have been cleaved with cyanogen bromide, which is specific for the carboxyl side of methionine residues, to release the desired hormone. This method is not suitable when the desired protein contains methionine residues.

Cleavage of fusion proteins by site-specific proteolysis has also been investigated. Fusion proteins into which a chicken pro α-2 collagen linker was inserted could be specifically degraded by purified microbial collagenase to release the components of the fusion protein. Other methods for purification and recovery of a desired recombinant protein include construction of a poly-arginine tail at the carboxyterminus of the protein. The arginine residues increase the overall basicity of the protein which facilitates purification of the desired protein by ion exchange chromatography. Subsequent removal of the poly-arginine tail by carboxypeptidase B regenerates the desired protein and allows purification from basic contaminants due to the reduction in pI of the desired protein.

It is of interest to develop a rapid and inexpensive method for purification or immobilization of a desired protein. Carbohydrate polymers such as cellulose are plentiful and inexpensive. Furthermore, a variety of enzymes bind specifically to carbohydrate polymers and polysaccharides. It would therefore be of interest to prepare fusion proteins comprising at least the carbohydrate polymer-binding portion of such an enzyme as a means for immobilizing and/or purifying the fusion protein using a carbohydrate polymer solid phase.

It is also of interest to attach various agents to the fusion protein which can give the fusion protein an additional characteristic, in combination with its ability to bind polysaccharide surfaces. Similarly, it is of interest to attach various agents to the carbohydrate polymer binding moiety itself to facilitate the binding of these agents to the carbohydrate polymer.

RELEVANT LITERATURE

The affinity of cellulases for cellulose have been used for their purification (Boyer et al., *Biotechnol. Bioeng.* (1987) 29:176–179; Halliwell et al., *Bio-chem. Chem J.* (1978) 169:713–735; Mart'yanov et al., *Biokhi-miya* (1984) 19:405–104; Nummi et al., *Anal Biochem.* (1981) 116:137–141; van Tilbeurgh et al., *FEBS Letters* (1986) 204:223–227). Several cellulase genes from *Cellulomonas fimi* have been cloned into *Escherichia coli* (Whittle et al., *Gene* (1982) 17:139–145; Gilkes et al., *J. Gen. Microbiol.* (1984) 130:1377–1384). Binding to Avicel (microcrystalline cellulose) has been used for purification of both native (Gilkes et al., *J. Biol.Chem.* (1984) 259:10455–10459) and recombinant enzymes (Owolabi et al., *Appl. Environ. Microbiol.* (1988) 54:518–523). A bifunctional hybrid protein which binds maltose has been described Bedouelle et al., *Eur. J. Biochem.* (1988) 171:541–549.

Two of the *C. fimi* cellulases, an exoglucanase (Cex) and an endoglucanase (CenA), have been characterized and their genes, cex and cenA, have been sequenced (Wong et al., *Gene* (1986) 44 315–324; O'Neill et al., *Gene* (1986) 44:325–330). Predicted amino acid sequences show evidence of domain structure for these enzymes (Warren et al., *PROTEINS: Structure, Function, and Genetics* (1986) 1:335–341). Domain structures have also been observed in other cellulases (Teeri et al., *Publications* (1987) 38: Technical Research Centre of Finland; Teeri et al., *Gene* (1987) 51:43–52) and separation of domains by proteolytic cleavage has given some insight into domain function (Langsford et al., *FEBS Letters* (1987) 225:163–167; Tomme et al., *Eur. J. Bio-chem.* (1988) 170:575–581; van Tilbeurgh et al., *FEBS Letters* (1986) 204:223–227).

A serine protease found in *C. fimi* culture supernatants (Langsford et al., *J. Gen. Microbiol.* (1984) 130:1367–1376) has been shown to cleave substrate-bound recombinant CenA and Cex, releasing catalytically-active fragments with greatly reduced affinity for cellulose (Langsford et al., FEBS Letters (1987) 225:163–167). The remaining fragments correspond to the irregular regions of low charge density in both enzymes and are believed to constitute the cellulose-binding domains of the enzymes. A detergent composition for clothing incorporating a cellulase has been described in U.S. Pat. No. 4,822,516 filed Dec. 2, 1987. Known hydrolytic disruption of cellulose fibers by the binding domain of a bacterial cellulase has been described in Din et al., *Bio/Technology* (1991) 9:1096–1099. A de-inking process for waste paper for recycling comprising pulping at high pH, then lowering the pH and adding alkaline cellulase has been described in WO 91/14819 published Oct. 3, 1991.

SUMMARY OF THE INVENTION

Compositions, together with methods for their preparation and use, are provided which comprise removable labels capable of binding to a polysaccharide. The removable labels comprise an amino acid sequence characterized as capable of binding to a polysaccharide and obtainable from a polysaccharidase conjugated to a heterologous protein or a chemical moiety. Optionally the chemical agent can be bound to a polypeptide. The label may be removed from a polysaccharide substrate by contacting the substrate with a removal solution having low ionic strength, high pH or containing a chaotrophic agent. Alternatively, a nonspecific protease may be used for enzymatic removal of the label following binding to a polysaccharide substrate. The invention finds use for generating removable markers, such as removable ink and removable tags for assays.

BRIEF DESCRIPTION OF THE DRAWINGS

FIG. 1 shows a consensus sequence for the cellulose binding domain. Amino acid sequence alignments of the cellulose-binding domains (CDBS) of *C. fimi* cellulases (CenA SEQ ID NO: 1, and Cex SEQ ID NO: 2), and the putative binding domains of MbCelA (an endoglucanase from *Microbispora bispora*), SEQ ID NO: 3, ClfX (part of the translated open reading frame of *Cellulomonas flavigena* gene fragment), SEQ ID NO: 4, PfegI (an endoglucanase from *Pseudomonas fluorescens* var. *cellulosa*), SEQ ID NO: 5, PfxynA (a xylanase from *P. fluorescens* var. *cellulosa*), SEQ ID NO: 6, and BfegII (an endoglucanase from *Butyivibria fibrisolvens*), SEQ ID NO: 7. Amino acid residues are indicated in single letter code. Bold upper case letters indicate homology with the CenA sequence; plain upper case letters indicate homologies occurring only within the other six sequences; lower case letters indicate absence of homology. * indicates the amino terminus of the mature enzyme. *** indicates a carboxyl terminus deduced from occurrence of stop codons in corresponding DNA sequences. - indicates a gap left to improve the alignment. Numbers refer to residues at the start and end of respective lines: CenA, Cex, and PfxynA residues are numbered from the start of the mature proteins; MbCelA, PfeaI and BfeaI are numbered from the start of the unprocessed polypeptides since the sites of leader peptide processing have not been determined; ClfX is numbered from the start of the *C. flavigena* gene fragment open reading frame.

FIG. 3 shows sequences of plasmids pUC12-1.1cex, SEQ ID NOs: 8, 9, 10 and 11, pUC12-1.1(737), SEQ ID NOs: 12 and 13 and pUC12-1.1(PTIS), SEQ ID NOs: 14 and 15, in the region of the ribosome binding site (RBS). The influence of the PTIS ribosome binding site is evident from the enzyme activities produced.

FIG. 7A shows fed-batch production, purification, and immobilization of the fusion protein. FIG 7B shows use of the fusion protein for hydrolysis of cellulosic materials to glucose with a reusable fermentor-immobilization column set-up.

FIGS. 10A–10C show construction of the expression vector pUC18-CBD.PT and structure of the CBD.PT gene. The construction of the expression vector by a three fragment ligation is shown in 10A. Fragment (i) was obtained by pUC18 by digestion with EcoRI and KpnI. A 1.6 kilobase SstI—SstI fragment containing cenA was excised from pUC18 1.6 cenA and used to prepare single-stranded DNA in M13mp18. A 24-base primer (5' CGT CGG CGT GGG GGT GGG GGT CGG 3', SEQ ID NO: 16), complementary to nucleotides 472–495 of cenA was hybridized to the single stranded DNA and extended. The single-stranded overhang was removed with mung bean nuclease and the double-stranded DNA cut with EcoRI to give fragment (ii); the region encoding the CBD is shown stippled and the regions encoding the P.T box (blunt end) and leader peptide are shown in black. Fragment (iii) was a synthetic blunt end-KpnI linker containing an internal EcoRI site. Ligation of fragments (i), (ii) and (iii) gave plasmid pUC18 CBD.PT (10B). The functional orientations of the β-lactamase (Amp$^r$) and lacZ, genes are indicated by arrows. The structure of the CBD.PT gene, SEQ ID NO: 19 and 20, is shown in 10C. The gene encodes the CBD, plus the PT box missing its C-terminal amino acid residue (Thr 165). The encoded amino acid sequence, SEQ ID NO: 21, is shown in single letter code, numbered from Met1 of the leader peptide. Leader peptide processing occurs between Ala28 and Ala29 and between Ala31 and Ala32.

FIG. 12A shows the equilibrium adsorption isotherms ([B] vs. [F] for CenA (solid triangle), CBD.PT$_{CenA}$ (solid square) and p30, the catalytic domain (solid diamond). Adsorption assays were done at 30° C., as described in the Experimental Procedures. The initial protein concentration range was 1.1–27.3 µM for CenA, 1.1–32.2 µM for CBD.PT$_{CenA}$ and 2.3–12.2 µM for p30. Each data point is the mean of six replicates; standard errors in two dimensions are indicated by vertical and horizontal bars. The inset shows the kinetics of adsorption of 3.4 µM (solid triangle) or 18.3 µM (open triangle) CenA, 3.4 µM (solid square) or 18.3 µM (open square) CBD.PT$_{CenA}$, and 18.3 µM p30 (open diamond). Each data point is the mean of six replicates; standard errors are indicated by vertical bars.

FIG 13A shows Scatchard plots ([B]/[F] vs. [B]) of the same data. Curved lines were fitted to data points of CenA (Solid line) and CBD.PT$_{CenA}$ (border line) by least squares regression analysis. In both types of plot, the standard errors in two dimensions are indicated by vertical and horizontal bars.

FIGS. 15A–15E shows adsorption of CBD$_{Cex}$ to cellulose and α-chitin. Avicel™ (5 mg) (15A), BMCC (1 mg) (15B), chitin (1 mg) (15C) or regenerated cellulose (1 mg) (15D) was mixed with varying initial concentrations of CBD$_{Cex}$ ([Po]=0.9–180 µM for Avicel™ and [Po]=1.8–300 µM for BMCC, chitin and regenerated cellulose). Saturation level (µMOL.g$^{-1}$) for each substrate is shown in FIG. 15E.

FIGS. 16A–16E shows relative affinities for the binding CBD$_{Cex}$ to cellulose and α-chitin. FIGS. 16A–16E are as described in FIGS. 15A–15E except that in 16E relative affinity (L.g$^{-1}$) for each substrate is shown.

DESCRIPTION OF THE SPECIFIC EMBODIMENTS

Figure 2:
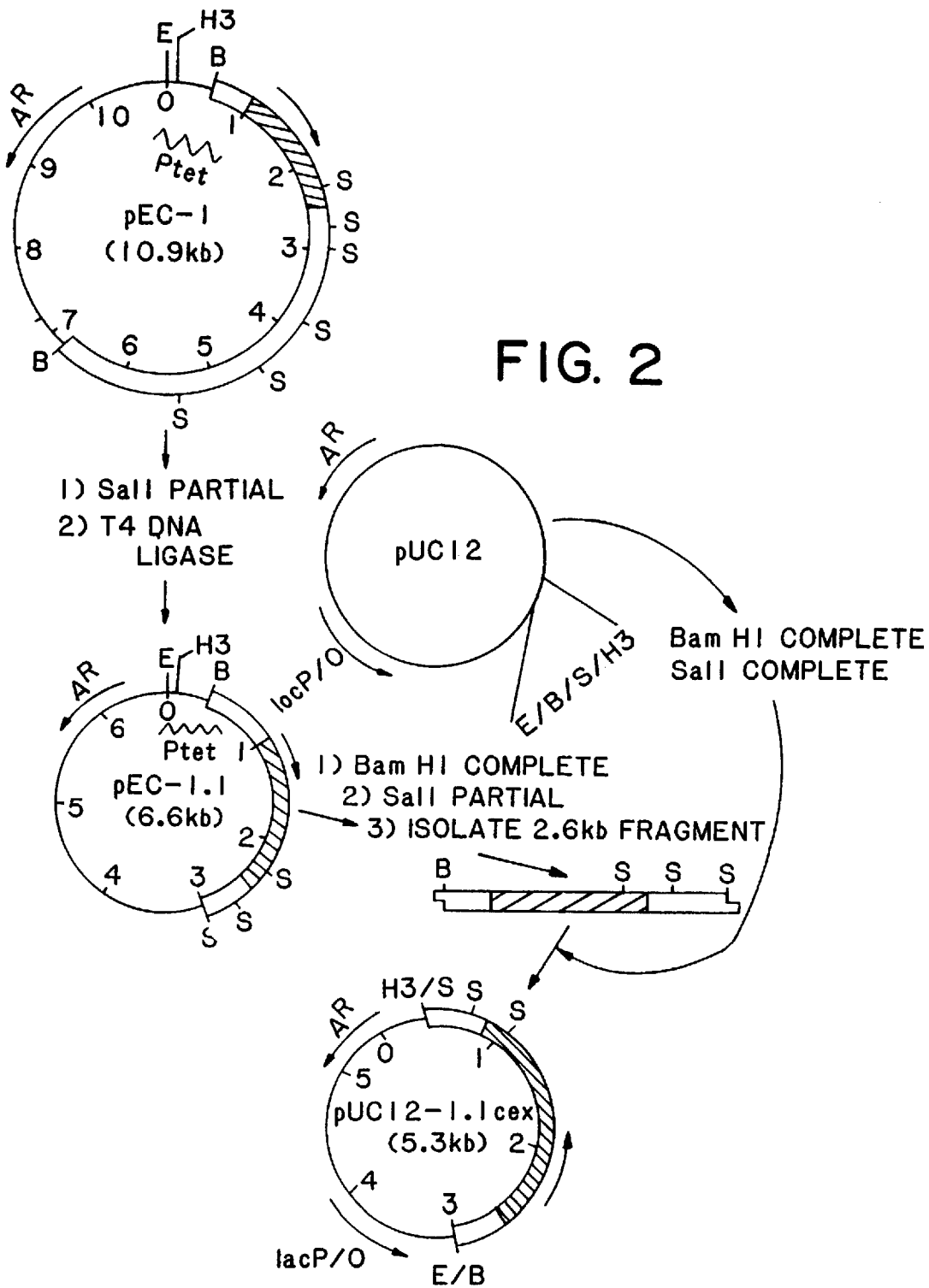
FIG. 2 shows construction of Cex-expressing plasmids pEC-1.1, and pUC12-1.1cex. The functional orientations of the gene coding for β-lactamase ($A^R$), Cex (a cross hatch square) and the promoters for lac are indicated by arrows. Restriction sites: B=BamHI; E=EcoRI; H3=HindIII; S=SalI.

Removable labels are provided which comprise an amino acid sequence obtainable from the polysaccharide binding-domain (PBD) of a polysaccharidase fused to a heterologous protein or conjugated to a chemical moiety. The amino acid sequence generally is essentially lacking in the hydrolytic enzymatic activity of a polysaccharidase, but retains the substrate binding activity. Methods for the preparation of polysaccharide binding domains are also provided, where the polysaccharide binding domain can be a polysaccharide binding domain of a polysaccharidase, a binding domain of a polysaccharide binding protein or a protein designed and engineered to be capable of binding to a polysaccharide. After binding to a polysaccharide substrate, the removable label can be removed from the substrate by contacting the substrate with a removal solution capable of eluting the label from the substrate or the label may be removed enzymatically by including a protease recognition site or chemical cleavage site between the label and the polysaccharide binding domain sites for collagenase, thrombin or Factor Xa which are cleaved specifically by the respective enzymes. Chemical cleavage sites sensitive, for example, to low pH or cyanogen bromide, may also be used. Alternatively, the entire polysaccharide binding peptide can be degraded by exposure to a relatively non-specific, general protease, such as protease K. Any of these procedures can be effective for the removal of the bound label.

The subject invention offers several advantages. The removable label provides a means for attaching a polypeptide or a chemical moiety to any substrate, soluble or insoluble, for the polysaccharidase. Additionally, the conjugate can be used to impart a desirable new physical property to a polysaccharide surface or matrix. Further, the selective binding of the polysaccharide binding domain of the chimeric compound and its characteristic of easy removal from the polysaccharide surface makes it especially suitable for the preparation of easily removable labels, dyes, coatings or tags from the substrate to which it is bound. As an example, a removable ink may be made which comprises a dye or a pigment conjugated to a cellulose binding domain (CBD) obtainable from a cellulase.

Current hydrocarbon based inks are difficult to remove. A common deinking treatment involves the addition of sodium hydroxide, sodium silicate, hydrogen peroxide and a detergent at pH10–11 and elevated temperature, for example, 40–50° C. to the substrate to be deinked. In contrast, CBD based materials bind specifically and strongly to paper but can be removed easily by elution with water or at high pH at ambient to physiologic temperatures, generally less than 40° C. and generally in the range of 20° C. Alternatively, the CBD-pigment can be removed by proteolysis using a general protease such as protease K at 30° C., pH 7.0. The CBD thus provides a means of attaching dyes or pigments to cellulose containing materials such as paper or cotton, which dyes or pigments later may be removed. As desired, the label may comprise up to the entire cellulase enzyme, including the protein having hydrolytic activity or may be essentially free of hydrolytic activity where a sequence including only the substrate binding domain is used. The latter is desirable were the integrity of the substrate is to be maintained. The former may find use where it is desired later to simultaneously break down the substrate and to remove the ink, e.g., as in recycling paper.

Novel polypeptide compositions can include those having the following formula:

PBD-MR-X               (1)

wherein:
    PBD can be either the N-terminal or the C-terminal region, or both, of the subject polypeptide and is characterized as having a sufficient amount of a consecutive sequence of amino acids from the substrate binding region of a polysaccharidase to provide for high affinity binding to a substrate of the polysaccharidase;

MR is the middle region, and can be a bond; short linking group of from 2 to 30 carbon atoms, or have from about 2 to about 20 amino acids. The region can include an amino acid sequence providing for specific cleavage of the fusion protein, usually a sequence corresponding to that recognized by a proteolytic enzyme of high specificities such as an IgA1 protease or Factor Xa; and X can be either the N-terminal or the C-terminal region and can be any peptide of interest or a chemical moiety. X is characterized as having up to the entire sequence of a polypeptide of interest, and can be an enzyme, a hormone, an immunoglobulin, a protein dye, etc.

Novel polypeptide conjugates compositions include those having the following formula:

$$PBD-Z \text{ or} \quad (2)$$

$$PBD-MR-Z \quad (3)$$

wherein:

the polysaccharidase binding domain (PBD) is characterized as (1) obtainable from the polysaccharidase binding domain of a polysaccharidase; (2) capable of binding to polysaccharides and optionally (3) is essentially lacking in polysaccharidase activity. The PBD is at least as large as the minimum number of amino acids in a sequence required to bind a polysaccharide; PBD-MR is defined as above; and Z is a chemical moiety that is attached to the polysaccharide binding domain. Z indicates only the moiety, not the stoichiometry of the moiety. The stoichiometry can be variable.

A variety of polysaccharide substrates are of interest. These include cellulose, a polysaccharide composed of D-glucopyranose units joined by β-1,4-glycosidic linkages and its esters, e.g. cellulose acetate; xylan, in which the repeating backbone unit is β-1,4-D-xylopyranose; chitin, which resembles cellulose in that it is composed of β-1,4-linked N-acetyl, 2-amino-2-deoxy-β-D-glucopyranose units. Enzymes that are capable of binding to polysaccharides, such as those listed above, are of interest in the subject invention as a source of amino acid sequences capable of binding to such substrates.

Several types of enzymes are involved in the microbial conversion of cellulose and xylan and include endoglucanases (1-4-β-D-glucan glucanohydrolase, EC 3.2.1.4); cellobiohydrolases (1,4-β-D-glucan cellobiohydrolase EC 3.2.1.91); β-glucosidases; xylanases (1,4-β-D-xylan xylanohydrolase, EC 3.2.1.8) and β-xylosidases (1,4-β-D-xylan xylohydrolase, EC 3.2.1.37). The compositions can be prepared by transforming into a host cell a DNA construct comprising DNA encoding at least a functional portion of the polysaccharide binding region of a polysaccharidase or a polysaccharide binding protein. A DNA sequence encoding a heterologous protein can be litigated to the PBD DNA sequence. The fused gene or the PBD DNA sequence alone, can be expressed in a host cell, either an eukaryotic or a prokaryotic cell. Expressed and isolated fusion proteins and PBD's then can be conjugated to chemical moieties.

The techniques used in isolating polysaccharidase genes and polysaccharide binding proteins, such as a cellulase gene are known in the art, including synthesis, isolation from genomic DNA, preparation from cDNA, or combinations thereof. Various techniques for manipulation of genes are well known, and include restriction, digestion, resection, ligation, in vitro mutagenesis, primer repair, employing linkers and adapters, and the like (see Maniatis et al., Molecular Cloning, Cold Spring Harbor Laboratory, Cold Spring Harbor, N.Y., 1982).

Generally, the method comprises preparing a genomic library from an organism expressing a polysaccharidase or polysaccharide binding protein with the desired characteristics. The proteins that interact with polysaccharides include lectins, chitinases and amylases, as well as xylanases and the beta-1,4 glycanases. Many of the enzymes which bind to polysaccharides comprise discreet catalytic and binding domains. However, the invention is not limited to the use of binding domains from such enzymes; those in which the binding and catalytic domains are one and the same may also be used.

Examples of enzymes which may be used in the subject invention are cellulases obtainable from strains belonging to the species of *Cellulomonas fimi, Trichoderma reesei* and *m. bispora*, and the like. The examples include xylanases from *P. fluorescens* subsp. *celluloses allulose* and *C. thermocellum*. The genome of the donor microorganism is isolated and cleaved by an appropriate restriction enzyme, such as BamHI. The fragments obtained are joined to a vector molecule which has previously been cleaved by a compatible restriction enzyme. An example of a suitable vector is plasmid pBR322 which can be cleaved by the restriction endonuclease BamHI.

The amino acid sequence of a polysaccharidase also can be used to design a probe to screen a cDNA or a genomic library prepared from mRNA or DNA from cells of interest as donor cells for a polysaccharidase gene. By using the polysaccharidase cDNA or a fragment thereof as a hybridization probe, structurally related genes found in other microorganisms can be easily cloned. Particularly contemplated is the isolation of genes from organisms that express polysaccharidase activity using oligonucleotide probes based on the nucleotide sequences of genes obtainable from an organism wherein the catalytic and binding domains of the polysaccharidase are discrete.

Figure 1:
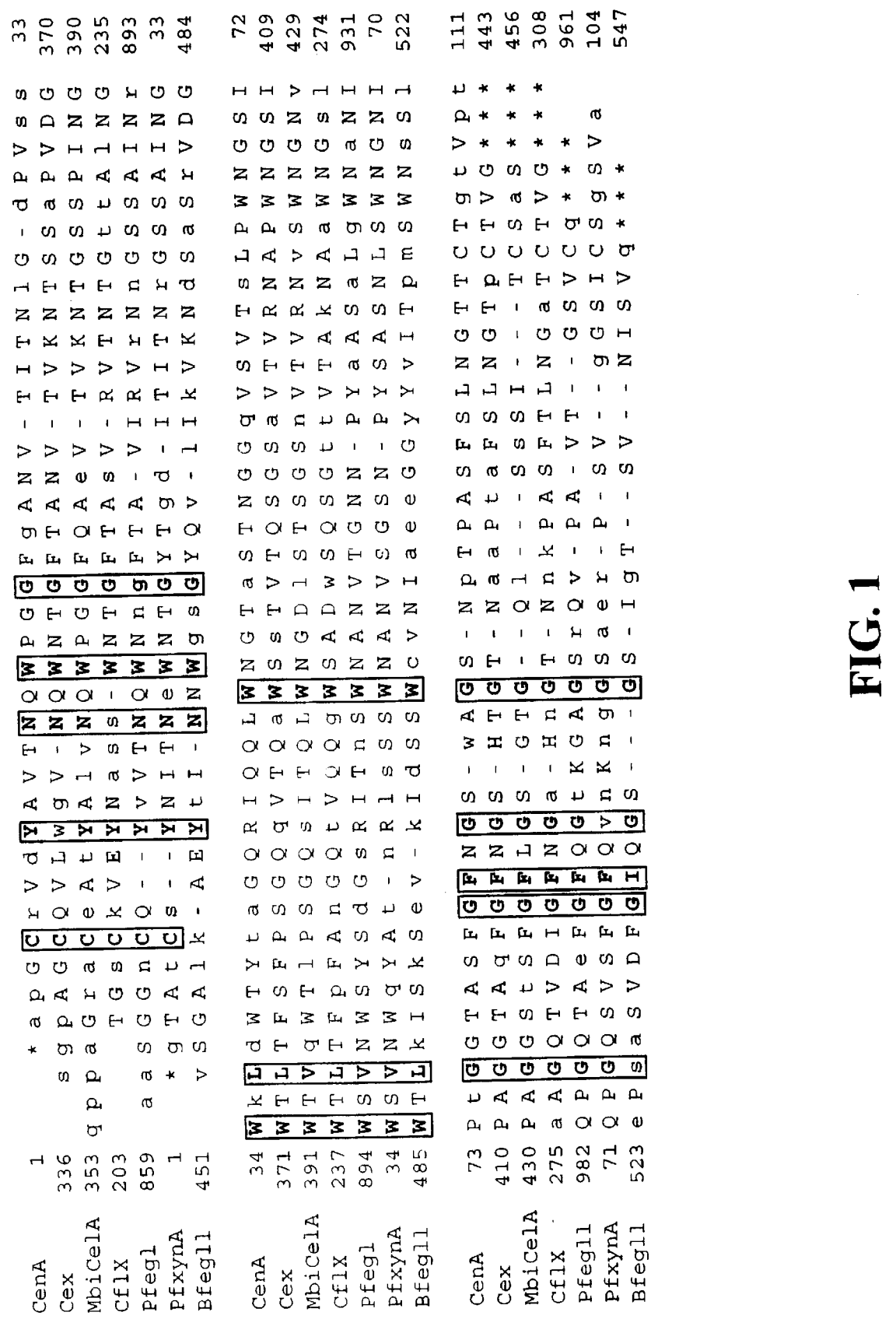

Probes developed using consensus sequences for the binding domain of a polysaccharidase are of particular interest. Exemplary of a consensus sequence of a binding domain is the consensus sequence for the cellulose binding domain shown in FIG. 1. The probes can be considerably shorter than the entire sequence but should be at least 10, preferably at least 14, nucleotides in length. Longer oligonucleotides are also useful, up to the full length of the gene, preferably no more than 500, more preferably no more than 250, nucleotides in length. RNA or DNA probes can be used.

In use, the probes are typically labeled in a detectable manner for example with $^{32}P$, $^{3}H$, biotin or avidin and are incubated with single-stranded DNA or RNA from the organism in which a gene is being sought. Hybridization is detected by means of the label after single-stranded and double-stranded (hybridized) DNA (or DNA/RNA) have been separated (typically using nitrocellulose paper). Hybridization techniques suitable for use with oligonucleotides are well known to those skilled in the art. Although probes are normally used with a detectable label that allows easy identification, unlabeled oligonucleotides are also useful, both as precursors of labeled probes and for use in methods that provide for direct detection of double-stranded DNA (or DNA/RNA). Accordingly, the term "oligonucleotide probe" refers to both labeled and unlabeled forms.

In order to isolate the polysaccharide-binding domain of a polysaccharidase or a polysaccharide binding protein, several genetic approaches can be used. One method uses restriction enzymes to remove a portion of the gene and then to fuse the remaining gene-vector fragment in frame to obtain a mutated gene that encodes a truncated protein. Another method involves the use of exonucleases such as Bal31 to systematically delete nucleotides either externally from the 5' and the 3' ends of the DNA or internally from a restricted gap within the gene. These gene deletion methods result in a mutated gene encoding a shortened protein molecule which can then be evaluated for substrate or polysaccharide binding ability. Appropriate substrates for evaluating and binding activity include Avicel, cotton fibers, filter paper, Kraft or ground wood pulp, and the like.

Once a nucleotide sequence encoding the polysaccharide binding region has been identified, either as cDNA or chromosomal DNA, it can then be manipulated in a variety of ways to prepare a removable label, where the removable label has a structure represented by formula (1) above the nucleotide sequence may be fused to a DNA sequence encoding a polypeptide of interest. The polysaccharide binding domain encoding fragment and the DNA encoding the polypeptide of interest are then ligated. The resulting ligated DNA can then be manipulated in a variety of ways to provide for expression. Microbial hosts can be employed which can include, for example bacteria such as *E. coli,* and eukaryotes such as Saccharomyces cerevisiae, or mammalian cells. Preparation and isolation of fusion proteins according to formula (1) are as follows.

Illustrative transcriptional regulatory regions or promoters include, for bacteria, the lac promoter, lambda left and right promoters, trp and lac promoters, tac promoter, and the like. The transcriptional regulatory region may additionally include regulatory sequences which allow the time of expression of the fused gene to be modulated, for example the presence or absence of nutrients or expression products in the growth medium, temperature, etc. For example, expression of the fused gene can be regulated by temperature using a regulatory sequence comprising the bacteriophage lambda PL promoter, the bacteriophage lambda OL operator and a temperature sensitive repressor. Regulation of the promoter is achieved through interaction between the repressor and the operator.

The expression cassette can be included within a replication system for episomal maintenance in an appropriate cellular host or can be provided without a replication system, where it can become integrated into the host genome. The DNA can be introduced into the host in accordance with known techniques, such as transformation, using calcium phosphate-precipitated DNA, transfection by contacting the cells with a virus, microinjection of the DNA into cells or the like.

Once the fused gene has been introduced into the appropriate host, the host can be grown to express the fused gene. In some instances, it can be desirable to provide for a signal sequence (secretory leader) upstream from and in reading frame with the structural gene, which provides for secretion of the fused gene. Illustrative secretory leaders include the secretory leaders of penicillinase, immunoglobulins, T-cell receptors, outer membrane proteins, and the like. By fusion in proper reading frame the chimeric polypeptide can be secreted into the medium.

Where the product is retained in the host cell, the cells are harvested, lysed and the product isolated and purified by binding to a polysaccharide substrate.

Where the product is secreted, the nutrient medium can be collected and the product isolated by binding to a polysaccharide matrix. To produce an active protein it can be necessary to allow the protein to refold. The recombinant products can be glycosylated or non-glycosylated, having the wild-type or other glycosylation. The amount of glycosylation depends in part upon the sequence of the particular peptide, as well as the organism in which it is produced. Thus expression of the product in *E. coli* cells results in an unglycosylated product, and expression of the product in insect cells generally results in less glycosylation than expression of the product in mammalian cells. Expression in yeast can result in hyperglycosylation.

In addition to producing fusion proteins from fused genes, the fusion protein can be made chemically. The substrate binding region or multiples thereof is produced on its own, purified and then chemically linked to the polypeptide of interest using techniques known to those skilled in the art. Methods of protein conjugation include use of glutaraldehyde to couple peptides to carrier proteins (*Reichlin Methods of Enzymology* (1980) 70:159–165).

Removable labels comprising a conjugate of a polysaccharide binding domain and chemical moiety (formulas (2) and (3) above) can be prepared as follows. The amino acid sequence capable of binding the substrate of a polysaccharidase can be obtained as described above, or by other means known to those skilled in the art. The chemical moiety then can be attached to the amino acid sequence obtainable from the polysaccharide binding domain by a variety of chemical methods including covalent modification, ionic bonding, hydrophobic bonding, hydrogen bonding, protein translation, protein expression or combination thereof. Where the catalytic domain remains bound to the binding domain, if desired, specific inhibitors of catalytic activity may be used to inactivate the catalytic unit without affecting binding.

Covalent modification reactions can involve terminal amines, sulfhydryl groups, azido groups and other commonly used biochemical covalent bonding reagents. Non-covalent modification reactions can involve anionic bonding, hydrophobic bonding, hydrogen bonding and other commonly used non-covalent bonding reagents. If the polysaccharide binding domain is sensitive to a particular covalent or ionic reagent, the essential residues that make up the polysaccharide binding domain can be protected by incubating the domain with a ligand capable of binding the domain during the modification reaction. This technique protects the polysaccharide binding domain from reacting with the chemical agents used to modify other parts of the domain.

The conjugation of a chemical moiety to the fusion protein can occur both in vivo and in vitro. Typically, reactions can be carried out in vitro but on occasion in vivo conjugation can occur in the form of glycosylation and the like. In vitro conjugation chemical reactions to modify the polysaccharide binding domain can be carried out while the domain is either bound to the polysaccharide matrix or free from the polysaccharide matrix. Examples include the use of gluteraldehyde conjugation as described by Reichlin (1980), supra to couple a protein of interest such as protein A to a polysaccharidase binding domain such as a cellulose binding domain. When the polysaccharide binding domain is bound to the matrix, it offers the advantage of protecting the site that actually binds to the matrix while leaving other residues to react with the chemical moiety.

If bonding of the chemical moiety to the polysaccharide binding domain results in a diminished capacity to bind the polysaccharide substrate, a reaction procedure requiring the presence of the polysaccharide matrix is preferred to retain the binding characteristics of the domain. Conjugation reactions can be carried out with fusion proteins when it is desired to obtain hetero-bifunctional properties of the fusion protein conjugate. For example, the fusion protein can comprise an enzyme such as alkaline phosphatase, β-glucosidase or trypsin and a dye such as Coomassie blue or amido black.

Depending on the use of the removable label, the chemical moiety can be selected from a variety of compounds, including dyes, chromophores, isotopic chemicals, proteins, fats, liquids, carbohydrates, pigments and the like. It is also desirable to use chemical moieties that are stable in both non-aqueous and aqueous environment. Thus, preferred are dyes, markers and tags that dry on polysaccharide matrices.

When it is important to reduce non-specific, background binding, reagents should be used that are easily removed from the reaction mixture. For example, reagents that do not bind to a polysaccharide matrix, by themselves, can be used to reduce non-specific, background binding. For example, a removable label can be passed over a polysaccharide matrix and the unreacted reagent washed through while the removable label comprising the polysaccharide binding domain-conjugate remains bound to the matrix. Alternatively, the conjugated polysaccharide binding domain can be removed from the unreacted reagent by centrifugal techniques using polysaccharide matrix beads where the supernatant can contain the reagent and the PBD-conjugate can be sedimented along with the polysaccharide matrix beads. Depending upon the particular protocol and the purpose of the reagent, the polypeptide or the PBD alone can be tagged with a conjugate or untagged. A wide variety of tags have been used which provide for, directly or indirectly, a detectable signal. These tags include radionuclides, enzymes, fluorescors, particles, chemiluminesors, enzyme substrates or co-factors, enzyme inhibitors, magnetic particles, dyes, etc. Various methods exist for attaching or linking the tags to the polypeptides or PBDs and are well known to those skilled in the art. For example, the polypeptide N-terminal amino groups can be derivatized to form a pyrolezone, while other free amino groups are protected, where the pyrolezone can then be contacted with various reagents to link a detectable signal generating moiety. Alternatively, labels can also be attached to the polysaccharide binding domain by using protein modifying reagents such as sulfhydryl or azido groups.

In general, the polysaccharide binding domain-conjugates (removable labels) can be bound to polysaccharide matrices at neutral pH in a medium ionic strength buffer of from about $10^{-3}$ M to about 1 M. Binding can be performed at temperatures from 4° C. to at least 70° C. depending on the conjugate. Binding is virtually instantaneous and the temperature is not critical. Once the PBD-conjugate is bound to the matrix, the matrix can be dried or remain in an aqueous environment.

The type of polysaccharide matrix can be considerably varied. Examples include, but are not limited to, cotton, wood, paper products, chitin and both living and non-living sources of polysaccharide matrices. A matrix is defined as a surface having a two-dimensional or three-dimensional geometry and can include filter disks, chromatographic resins and the like. Such a conjugate can be used as selective tags to indicate where polysaccharides are located on various surfaces and as removable dyes and stains of polysaccharide surfaces both from synthetic and non-synthetic sources, such as cotton, rayon, wood, cellophane or paper. Conjugates can also be used to couple chemical agents such as antibiotics, fungicides, insecticides, texturizing agents, to such polysaccharide surfaces.

To debind the PBD conjugate from the matrix, a low ionic strength buffer or water is required or a buffer of alkaline pH or a chaotrophic salt. The temperature for desorption is not critical and generally in the range of 10° C.–40° C., although ambient temperatures are generally preferred, i.e., about 20° C. The bound PBD conjugate is washed repeatedly in water or diluted by a continuous stream of water. Generally, pH 9.5 a carbonate buffer or 6 M guanidine HCl can be used for this desorption step. Dilute sodium hydroxide (about 0.1 M) may be the preferred treatment in some cases. The nature of the PBD can be modified to alter its adherence properties so that it can be, or, if desired, cannot be, desorbed by water. Application of the desorption medium to the matrix causes the polysaccharide binding domain of the fusion protein to release the PBD-conjugate from the matrix.

This ease of debinding is in contrast to the method described in, for example, WO91/14819, in that using a PBD conjugate, enzymatic treatment of the polysaccharide surface is not required prior to deinking. Partial hydrolysis of the surface layer of the polysaccharide, e.g., with an alkaline cellulase, as described in WO91/14819, weakens the fibre structure, whereas in contrast, treatment of the polysaccharide with desorption solutions as described above does not alter the surface structure of the polysaccharide. Additionally, the alternative procedure involving the use of a non-specific protease to debind the PBD conjugate from a matrix acts directly on the conjugate and does not modify the polysaccharide surface.

For separation of the PBD-conjugate following release from the substrate, various techniques may be used. For example, the polysaccharide surface can be washed free of the PBD-conjugate with the desorption solution as described above. The PBD-conjugate can be separated from the desorption solution for example by changing its ionic strength of pH and readsorbing the PBD-conjugate on an ion exchange medium or on a polysaccharide matrix. The protein of interest or chemical moiety can be cleaved readily from the polysaccharide binding region by the use of a protease specific for a sequence present between the polysaccharide binding region and the protein of interest or the chemical moiety.

Cleavage of the binding domain from the recombinant protein of interest can be done in solution or while the fusion protein is immobilized on the polysaccharide matrix. In the latter case, the recombinant protein of interest or chemical moiety is released from the polysaccharide matrix free of contaminating polysaccharide binding domains. Alternatively, a non-specific protease can be used to completely degrade the PBD portion of the PBD complex, thus releasing it from the polysaccharide, for example, by treatment by protease K at a concentration of about 50μg/ml for about 20 minutes at about 37° C. Use of Fusion Proteins and PBD Conjugates The fusion proteins and PBD conjugates provide for a wide variety of applications including purification of the protein of interest, immobilization of the protein of interest, and preparation of solid phase diagnostics, purification of PBD conjugates, and the preparation of coatings, tags and removable dyes. Other applications can include binding a compound of interest to a polysaccharide matrix. The removable labels can be used also as a means of purifying compounds, particularly biological compounds. Examples of biologicals which can be purified in this way include interleukin 2, Factor X, ligninase, and TPA. Examples of PBD conjugates which could be purified in this way include PBD labeled with Coomassie blue, FITC (fluorescein isothiocyanate), and $I^{125}$.

The subject compositions can also be used as a means of immobilizing a fusion protein on a polysaccharide support, since the polysaccharide binding domain adsorption to its substrate is strong and specific. The immobilized systems find use, for example, in preparing solid state reagents for diagnostic assays, the reagents including enzymes, antibody fragments, peptide hormones, etc.; drug binding to decrease clearance rate where the cellulose can be either soluble, for example carboxymethyl cellulose or a solid support such a microcrystalline cellulose (Avicel) where the drug is a polypeptide such as interleukin 2; drug delivery, for example bound to carboxymethyl cellulose and can be used in conjunction with binding of an adjuvant to the same cellulose support for example for enhancement of immunospecificity of the drug to be delivered; dye binding, for example coupling of paints or dyes to polysaccharide, for example cellulosic surfaces; printing on for example paper and cloth (cotton); and to provide hydrolysis or synergy, for example targeting of enzymes such as ligninase for treatment of wood chips, targeting of porphyrins, for example for bleaching of wood pulp; agricultural uses such as binding of insecticides to plant surfaces, for example Bt toxin or other antimicrobials; for nitrogen fixation, for example for binding of organisms to root surfaces; sustained fertilizer release; and sustained release of fungicides; they can also be used under conditions of high salt such as in a marine environment for anti-fouling of surfaces exposed to sea water where transfer to fresh water removes the fusion protein.

The following examples are offered by way of illustration and not by way of limitation.

EXPERIMENTAL

Abbreviations pNPC=p-nitrophenyl-β-D-cellobioside;

HPA hide powder axure; gCenA and gcex=the glycosylated forms of CenA and Cex from *C. fimi*;

ngCenA and ngCex=the non-glycosylated forms of CenA and Cex from recombinant *E. coli*;

RPC=reverse-phase chromatography;

SDS-PAGE=sodium dodecyl sulfate-polyacrylamide gel electrophoresis;

α-Pro/Thr=rabbit antiserum directed against synthetic Cex Pro/Thr box;

PMSF=phenyl-methylsulfonyl fluoride.

Biological Culture Deposits.

The following deposits have been made with the American Type Culture Collection (ATCC), 12301 Park Lawn Drive, Rockville, Md., 20852:

(1) A derivative of the cloned gene CenA on plasmid pcEC-2 in *Escherichia coli* C600, deposited on Apr. 23, 1986 (ATCC Accession No. 67101); (2) a derivative of the cloned gene Cex on plasmid pEC-1, deposited on May 27,1986 (ATCC Accession No 67120); (3) *E. coli* JM83, pUC12-1.1cex, deposited on Apr. 23,1986 (ATCC Accession NO. 67102).

EXAMPLE 1

Construction of Cex Expression Plasmids

A. Bacterial Strains and Plasmids

The host strain C600 (thr-1 leu-6 thi-1 supE44 lacvY1 tonA21) and the plasmids pcI857 and pCP3 were obtained from Erik Remaut and are described in *Gene* (1983) 22:103–113.

B. Recombinant DNA Techniques

DNA preparations and enzyme reactions were performed as described by Maniatis et al., *Molecular Cloning: A Laboratory Manual,* Cold Spring Harbor Laboratory, Cold Spring Harbor, N.Y. Restriction endonuclease, DNA polymerase I (Klenow fragment), T4 DNA ligase, and the portable translation initiation site (PTIS) were purchased from Pharmacia Inc. Bacterial transformations of plasmids containing the leftward promoter (pL) of bacteriophage lambda into strains carrying the cI857 gene of phage lambda were carried out by the method of Maniatis et al., supra, except for the following modification. The bacterial cells were heat shocked at 34° C. for 2 min, incubated in LB medium for 1 hr, and then plated on selective medium.

C. Growth and Induction of Bacteria

Bacteria were grown in LB (Maniatis, supra) medium with the addition after autoclaving of 0.4% glucose, 50 μg of kanamycin per ml, and 75 μg of ampicillin per ml. After growth at 30° C. to an optical density at 600 nm of 0.3, the cultures were divided, and parallel samples were grown at 30° C. noninduced) and at 41° C. (induced).

D. Isolation of the cex Gene

The cex gene from *C. fimi* was isolated as described in U.S. patent application Ser. No. 06/859,042, filed May 2, 1986, now abandoned, which disclosure is incorporated herein by reference.

E. Plasmid Constructions 1. pUC12-1.1cex.

The cex gene was cloned on a 6.6-kilobase-pair (kbp) BamHI fragment of *C. fimi* DNA ligated into the BamHI site of pBR322, giving pEC-1 (See FIG. 2). The cex gene was localized by deletion analysis to a 2.56-kbp BamHI-SalI DNA fragment yielding pEC-1.1 (FIG. 2). The plasmid pUC12-1.1cex (FIG. 2) contains the 2.56kbp fragment from pEC-1.1 positioned in opposite orientations downstream from the promoter-operator region of the *E. coli* lactose operon (lacZp/o) in the plasmid pUC12 (Gene (1982) 19:259–268). The plasmid pEC-1, was described by Whittle et al., *Gene* (1982) 17:139–145 and Gilkes et al., *J. Gen. Microbiol.* (1984) 130:1377–1384, which disclosures are incorporated herein by reference.

2. pUC12-1.1(737).

For the construction of pUC12-1.1(737), the 5' untranslated sequences, the ribosome binding site (RBS), and the initiating codon of the cex gene were first removed and replaced with the promoter operator region, the RBS, and the amino terminus of (Gal) from the *E. coli* lac operon and then with the RBS-ATG sequences of the PTIS. In the first step, pUC12-1.1cex was cut with StyI and BamHI, the staggered ends were repaired with DNA polymerase I (Klenow fragment), and the plasmid DNA was ligated under dilute conditions to give pUC12-1.1(737). This manipulation results in (i) the in-frame fusion between codon 2 of the Cex leader sequence and codon 11 of the alpha-fragment of BGal encoded by pUC12; (ii) the regeneration of the StyI cleavage site; and (iii) the replacement of the cex initiating codon with a BamHI cleavage site. The nucleotide sequence and deduced amino acid sequence of the β-Gal-cex fusion region of pUC12-1.1(737) are shown in FIG. 3.

3. pUC12-1.1(PTIS).

To obtain pUC12-1.1(PTIS), pC12-1.1(737) was cut with EcoRI and BamHI, and the 17-bp PTIS with an EcoRI and a BamHI cohesive end was inserted. This procedure resulted in the in-frame fusion of the second codon of the cex leader sequence to the initiator ATG of the PTIS. (See below and FIG. 3):
PTIS

PTIS

AATTTGGAAAAATTATG (SEQ ID NO: 17)

ACCTTTTTAATACCTAG (SEQ ID NO: 18)

pUC12-1.1cex codes for unfused cex gene products. The numbering of the codons of the natural cex gene product in pUC12-1.1cex begins with the initiating ATG of the leader sequences as −41 and the first codon of the mature cex as +1. The first cex codon in the β-Gal-Exg fusions retains its original position number. The deduced amino acid sequence is shown in single-letter code over the DNA sequence. The nucleotides and amino acids derived from β-Gal are underlined. Lower-case amino acids are of non-lac origin and are derived from the linker region in pUC12. The restriction sites StyI, AvaII, and EcoRII in the amino terminus of the cex gene were used for fusion of the cex gene to the amino terminus of BGal in pUC12. Cex activity is expressed as nanomoles of p-nitrophenyl released per minute per milligram of total cell protein.

EXAMPLE 2

Construction of CenA Expression Plasmids

A. Bacteria and Medium

E. coli JM101 was used for all cenA experiments. All cultures were grown on LB medium, solidified with 1.5% (w/v) agar when necessary. Ampicillin was added at a final concentration of 100 $\mu$/ml. CenA activity was detected by staining with Congo red after growth of colonies on LB containing 1.0% (w/v) agar and 1.0% (w/v) carboxymethyl cellulose (CMC). Liquid cultures were 10 or 50 ml in 50 or 250 ml Erlenmeyer flasks; they were grown in a New Brunswick Gyrotory water bath at 200 rpm.

B. DNA Techniques

Plasmids were released from E. coli by alkaline lysis and purified by centrifugation to equilibrium in CsCl-ethidium bromide gradients. Digestion with restriction endonucleases, ligation of fragments and transformation of E. coli were performed as described.

C. Other Methods

Extracts were prepared by rupturing the cells with a French press. Enzymes were released from the periplasm by osmotic shock. Culture supernatants were obtained by centrifugation. All enzymes were assayed at 30° C. Endoglucanase from E. coli JM101/pUC18-1.6 cenA was purified by immunoadsorbent chromatography, followed by anion exchange chromatography on Mono Q resin with a gradient of 0–1.0 M NaCl in 20 mM piperazine, pH 9.8. Amino acid sequencing was by automated Edman degradation using an Applied Biosystems 470A gasphase sequenator.

D. Isolation of the CenA Gene

The CenA gene from C. fimi was isolated as described in U.S. patent application Ser. No. 07/630,396 filed Dec. 18, 1990, now abandoned, as a continuation of U.S. patent application Ser. No. 06/94,326 filed Aug. 7, 1986, now abandoned.

E. Plasmid Construction

Figure 4:
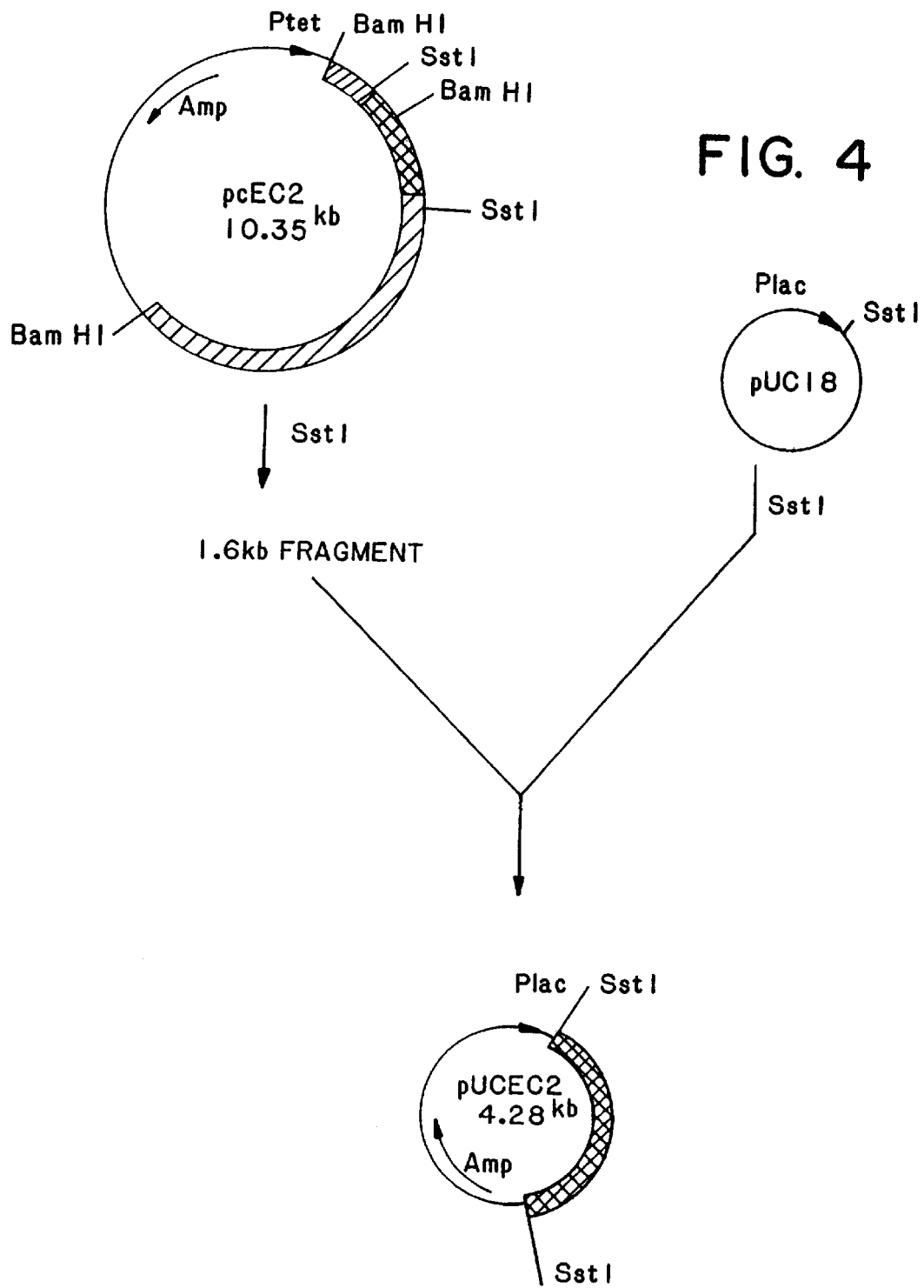
FIG. 4 shows a construction of pUCEC2.

A 1.6-kb SstI fragment from the 6.0-kb insert of C. fimi DNA in pcEC2 was purified and sub-cloned into the SstI site of pUC18 to form pUCEC2, a schematic representation of which is shown in FIG. 4. The line represents BR322 DNA; the box is C. fimi DNA; the hatched area is the cenA coding sequence; the arrow shows the direction of transcription; S is SstI; A) pcEC2; (B) the nucleotide and amino acid sequences at the fusion point of lacZ and cenA in pUCEC2.

EXAMPLE 3

Figure 5:
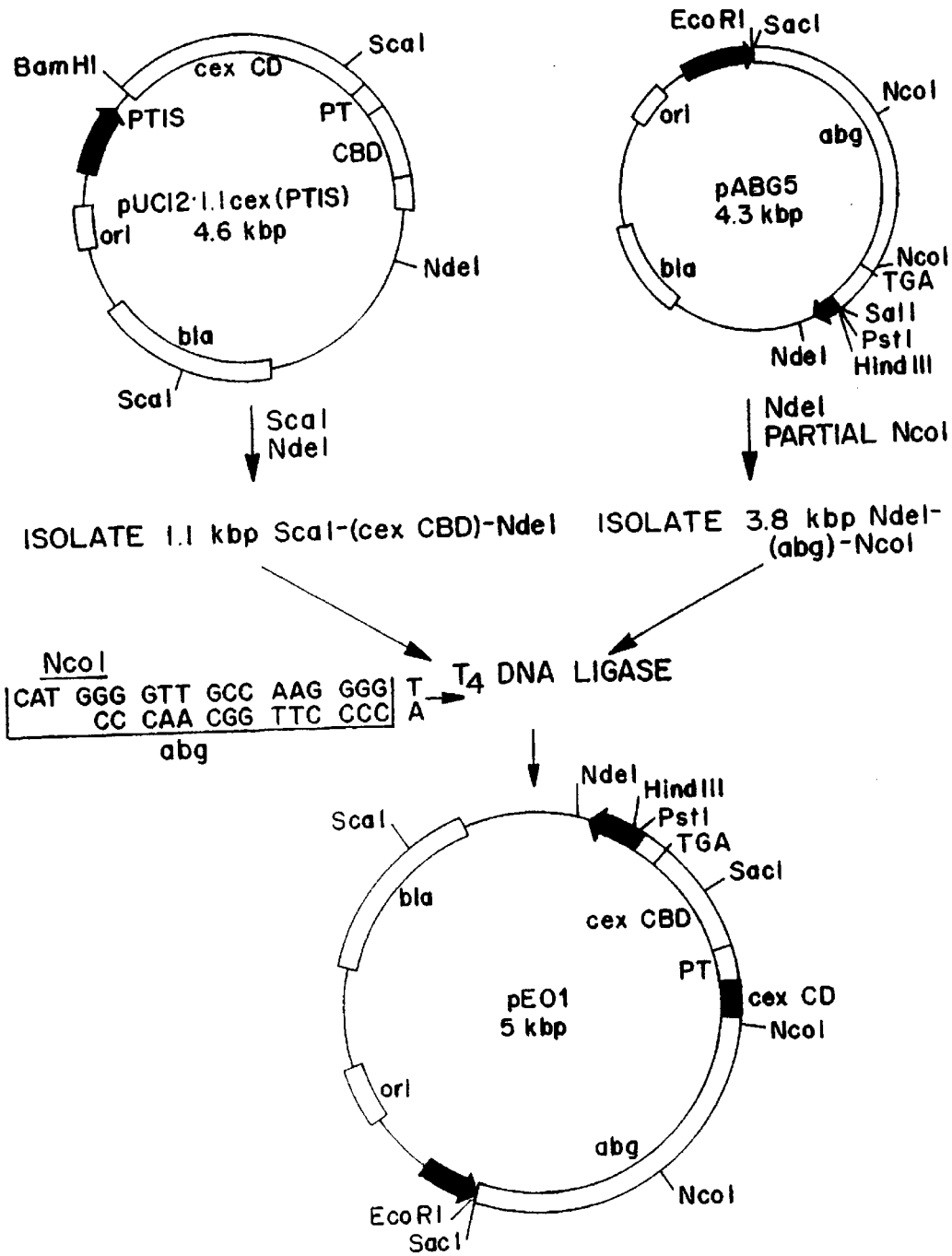
FIG. 5 shows construction of pEO1. pUC12-1.1cex. (PTIS) was digested completely with ScaI and NdeI, and the 1.1 kbp fragment was isolated containing the cex CBD coding sequence. pABG5 (Wakarchuk et al. (1986) was first digested completely with NdeI then partially with NcoI. A 3.8 kbp fragment containing the whole vector sequence plus the sequence encoding all but the last six amino acids of Abg was isolated. The 1.1 kbp and 3.8 kbp fragments were ligated using an adapter which encoded the last six amino acids of Abg to give pEO1.

Construction of Expression Vector Containing Fusion of cex SBD Gene Fragment and Agrobacterium β-glucosidase Gene (abg) and Characterization of Fusion Protein A. Construction of Vector Plasmid pUC12-1.1cex (PTIS) was cut to completion with ScaI and NdeI (see FIG. 5). The 1.1 kbp fragment was isolated containing the cex CBD coding sequence. pABG5 (Wakarchuk et al., 1986) was first digested completely with NdeI then partially with NcoI. A 3.8 kbp fragment containing the whole vector sequence plus the sequence encoding all but the last six amino acids of Abg was isolated. The 1.1 kbp and 3.8 kbp fragments were ligated using an adapter which endoes a last six amino acides of Abg, to give pEO1.

Plasmid pEO1 corresponds to a vector which is 2700 bp and the fused cex CBD-abg insert which is 2254 bp. The plasmid construct is transformed into E. coli JM109.

B. Enzymatic and PAGE Characterization of the Fusion Protein

The fusion protein encoded by pEO1 is characterized for its catalytic activity compared to the original Abg and for its ability to bind to Avicel compared to the original Cex. Characterization of catalytic activity includes determination of the kinetic properties (e.q., $k_m$ and $V_{max}$) and substrate specificity of the fusion enzyme. Enzyme activity is determined by the amount of glucose produced from a fixed concentration of cellobiose under standard assay time, temperature, pH, ionic strength and buffer. The glucose concentration is measured using a glucose analyzer (Beckman). The analysis is based on the initial rate of oxygen consumption in the conversion glucose to gluconic acid as determined by an oxygen electrode; the rate of oxygen consumption is directly proportional to the amount of glucose present relative to a known standard glucose solution. The fusion protein is also analyzed by SDS-PAGE to determine relative molecular mass. The purified fusion protein can be cleaved with the protease from C. fimi to produce two or more other protein fragments. This is ascertained by running an SDS-PAGE of a proteolytic cleavage mixture of the fusion protein and doing a zymogram using a fluorescent glucoside derivative, MUG (4-methylumbelliferyl-β-D-glucoside) or X-glu (5-bromo-4-chloro-3-indolyl-$\xi$-D-glucopyranoside). This also determines whether other smaller active enzyme fragments are formed and their relative sizes.

C. Characterization of the Adsorption Properties of the Fusion Enzyme

Adsorption of cellulase to cellulose is presumed to be the first step required in the hydrolysis of insoluble cellulosic substrates. Enzyme binding to cellulose has been investigated for a few microbial cellulases with the aim of understanding how factors like enzyme concentration, enzyme, combination and ratio, temperature, pH and ionic strength of buffer might affect the adsorption kinetics of cellulase and the rate of cellulose degradation (Ghose & Bisaria, 1979; Moloney & Coughlan, 1983; Ooshima et al., 1983; Ryu et al., 1984; Andrease et al., 1987; Williamson & Stutzenberge, 1987).

The adsorption of a ligand (CenA, $CBD.PT_{CenA}$, Cex, or $CBD_{Cex}$) is assumed to be an equilibrium reaction in which a single ligand reacts with one or more of the repeating cellobiose lattice units on the surface of crystalline cellulose. At equilibrium, the adsorption reaction is described by $$K_a = \frac{[B]}{[N][F]} \quad (1)$$

where [B] is the concentration of bound ligand (mol.g cellulose$^{-1}$), [F] is the concentration of free ligand (molar), [N] is the concentration of available binding sites (mol.g cellulose$^{-1}$) and $K_a$ is the equilibrium association constant (1.mol$^{-1}$).

If a single ligand interacts with only one lattice unit and there are no positive or negative co-operative effects.

$$[N]=[N_o]-[B] \quad (2)$$

where $[N_O]$ is the concentration of binding sites in the absence of ligand. Substitution of equation (2) into equation (1) and rearrangement yields the Langmuir equation:

$$B = \frac{[N_o]K_a[F]}{1+K_a[F]} \quad (3)$$

However, the dimensions of the CBD greatly exceed the dimensions of the repeating cellobiose lattice unit on the cellulose surface; therefore, the ligand must occupy several lattice units. If a binding site is larger than one lattice unit, the surface must be considered as an array of overlapping potential binding sites. Under these conditions, [N] is described by a probability function which depends not only on [B] but also on the configuration of bound ligands on the cellulose surface (see Discussion). To avoid this complication, it is appropriate to consider adsorption at only very low values of [B] where ligands are spaced such tat any two nearest ligands do not exclude the binding of a third ligand. Under these conditions, equation (2) may be rewritten as $$[N]=[No]-\alpha[B] \quad (4)$$

where a is the number of lattice units occupied by a single ligand molecule. Substitution of equation (4) into equation (1) and rearrangement yields $$[B] = \frac{[N_o]K_a[F]}{1+aK_a[F]} \quad (5)$$

Data obtained at low ligand concentrations may be fitted to this equation. It is convenient to plot the adsorption data using the double reciprocal form of equation (5):

$$\frac{1}{[B]} = \frac{1}{K_a[N_o]} \cdot \frac{1}{[F]} + \frac{\alpha}{[N_o]} \quad (6)$$

which emphasizes data for the lower concentration range. The slope (1/$K_a$[$N_o$]) and intercept ($\alpha$/NO]) of a plot of 1/[B] vs.1/[F] were estimated by fitting a straight line through data points for low values of [B]. Unique solutions for $K_a$,[N], or $\alpha$ cannot be obtained from this analysis but a relative equilibrium association constant, $K_r$ (1.g cellulose$^{-1}$), where $$Kr=[N_O]K_a \quad (7)$$

can be used to compare the affinities of various related ligands for a given preparation of cellulose (i.e. when $[N_O]$ is constant). A doubly weighted least squares analysis was used because error occurs in both the 1/[B] and 1/[F] dimensions. In this method, residuals are weighted along both axes when minimizing the sum of squares errors between the fitted line and data points. The value obtained for $K_r$ is important in it measures the adsorption affinity of the enzyme to the substrate and the number of adsorption sites per unit surface of the adsorbent, respectively. The $K_r$ value in particular is needed so that meaningful comparisons of the effects of different physical and chemical parameters on the adsorption of the fusion enzyme to cellulose can be made.

The ability of the enzyme to bind to Avicel is expressed as the percentage enzyme bound relative to the known activity concentration of the enzyme introduced into the system, of the free enzyme present in the supernatant fluid and of the bound enzyme eluted from substrate with distilled water. Kinetic studies on the adsorption process of the enzyme towards cellulosic substrate at varying enzyme concentration includes the determination of $K_r$ at different pH, temperature and ionic strength of the buffer. Stability (operational and storage) of the immobilized fusion protein is determined by binding the enzyme to Avicel in batch or column and allowing enzymatic reaction to occur as a function of time. The amount of glucose recovered, the activity concentration of the fusion protein and the amount of protein in the eluent versus time indicates the stability of the immobilization scheme.

EXAMPLE 4

Isolation of DNA Fragment Responsible for Substrate Binding

To define the specific SBD peptide involved in substrate binding, several genetic approaches are available. One method uses restriction enzymes to remove a portion of the gene and then to fuse the remaining gene-vector fragment in-frame to obtain a mutated gene that encodes a protein truncated for a particular gene fragment. Another method involves the use of exonucleases (e.g., Bal31) to systematically delete nucleotides either externally from the 5' and the 3' ends of the DNA or internally from a restricted gap within the gene.

These gene deletion methods have the ultimate goal of producing a mutated gene encoding a shortened protein molecule, whose function may or may not be the same as the original protein molecule. Alteration of function in the truncated protein can be as a result of either the removal of that particular peptide fragment per se or from conformational changes in the modified protein as a result of deletion of some amino acids.

A. Deletion Using XmaIII Restriction Enzyme

Figure 6:
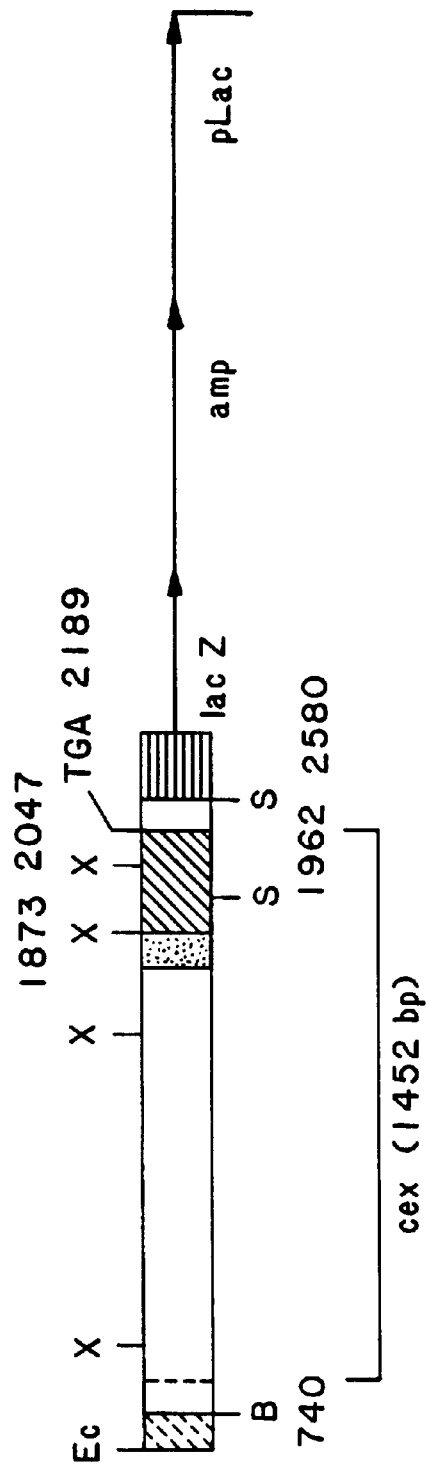
FIG. 6 shows the coding region for the exoglucanase Cex in PUC 12-1.1cex (PTIS). Restriction sites used in the generation of deletion mutants in the ~8 KDa cellulose binding domain are indicated by nucleotide number and are defined in the text of Example 4.

The region of the plasmid pUC12-1.1cex (PTIS) which codes for the *Cellulomanas fimi* exoglucanase Cex is shown in FIG. 6 with the relevant restriction sites and sizes.

Initial binding studies of a SalI (S) partial digest of the plasmid eliminating that portion of the gene between nucleotide (nt) 1962 and nt 2580 have shown that the resulting truncated protein did not bind to Avicel. This result does not prove that the peptide encoded between the SalI site (nt 1962) to the stop codon (TGA at nt 2189) is the essential region for binding of the enzyme. The region just before the start of the deletion could have well been an important region for binding to cellulose. Another factor that could have contributed to the nonbinding to cellulose by the SalI deletion mutant is the formation of a fusion protein between the deleted Cex and the β-galactosidase of the vector.

Assuming an amino acid has an average molecular weight of 110, the deleted peptide in the SalI mutant is approximately 8 kD in size. This predicted size corresponds well to the size of a peptide that was purified by FPLC (Pharmacia) from a sample of proteolytically cleaved exoglucanase and that was subsequently found to bind tightly to Avicel. This result strongly suggests that the specific SBD peptide is within this apparent 8 kD region. The N-terminus of the FPLC purified approximate 8 kD peptide has been sequenced to determine exactly where the proteinase cleavage site is. Results indicate that the amino acid cleavage site occurs at the end of the PT box (between the last threonine and serine). Based on this amino acid sequence result. The calculated size of the SBD peptide should have been 11.3 kD. This discrepancy between the size of the FPLC purified SBD peptide and the calculated size as predicted from the amino acid cleavage site could have arisen from an aberrant migration of the peptide on the polyacrylamide gel.

To delineate further the amino acid sequence involved in substrate binding, the plasmid pUC12-1.1cex is digested partially with XmaIII. The linearized fragment corresponding to 5107 bp in size is isolated, relegated and transformed into *E. coli* JM101. The gene portion between nt 1873 and nt 2074 is deleted and the remaining gene-vector is fused back together in-frame. The truncated protein produced and its binding affinity for Avicel is characterized and compared to the original cex protein.

B. Deletion Using Bal31

Bal31 is a highly specific nuclease that simultaneously degrades both the 3' and 5' ends of dsDNA without internal single-stranded cuts. Since there is an absolute requirement of the enzyme for $Ca^{++}$, the extent of deletion by the enzyme can be monitored and controlled by simply adding a divalent chelating agent, EGTA to the reaction mixture (Maniatis et al., 1982).

Before submitting the cex gene to Bal31 digestion, a loopout fragment containing the following regions is synthesized: 1) a restriction site where deletion starts (XbaI which is only found in the vector and just a few nucleotides downstream of the *C. fimi* gene insert); 2) a second restriction site not found in either the vector or the insert (NcoI); 3) a stretch of nucleotides containing stop codons in all three reading frames.

The loopout fragment is first annealed to a M13 ssDNA template containing the insert. The fragment is extended by adding d(A,T,G and C)TPs, Klenow polymerase and ligase. This fragment is transformed into *E. coli* JM101 and the plaques hybridizing with the labeled loopout primer are picked up. The replicative form of DNA is isolated from the *E. coli* transformants. The duplex DNA is first cut with XbaI to linearize DNA. The same linearized DNA is then cut with NcoI. A stuffer DNA fragment containing *C. fimi* DNA flanked at one end with an NcoI site is also cut with NcoI. The stuffer DNA is ligated to the linearized DNA to regenerate an NcoI site. This construct is then digested with Bal31 which digests from both ends (in the stuffer DNA and in the cex gene insert) at almost the same rate. The reaction mix is stopped periodically by removing a portion of the reaction sample and putting it into DNA buffer containing EGTA to stop Bal31 digestion. The stuffer DNA is removed by adding NcoI to the inactivated Bal31-digested DNA mixture. The DNA is then filled in with Klenow polymerase, size fractionated in an agarose gel and blunt ligated to pUC12 to obtain a closed, circular, duplex DNA. A few microliters from the ligated mix is then cut with two restriction enzymes in such a way that small differences in the insert length as a result of deletion by Bal31 can easily be ascertained. The DNA is transformed into competent *E. coli* JM101 cells. To screen for a family of mutants deleted at the 3 end of cex antibody raised against the apparent 8 kD SBD peptide is used to identify positive deletion clones.

Truncated proteins produced from the different deletion mutants are tested for their ability to bind to Avicel and for their catalytic activity as described above.

EXAMPLE 5

Figure 7A:
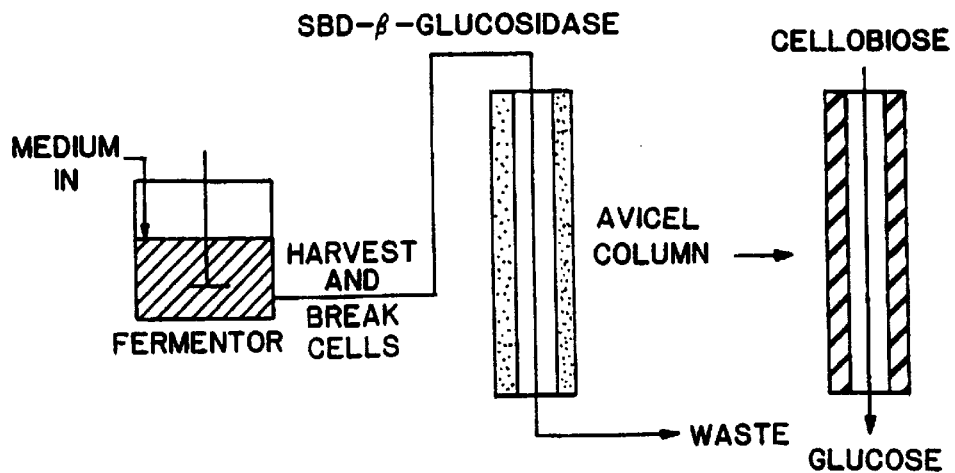
FIGS. 7A and 7B are schematic diagrams for immobilization and use of the fusion protein.
Figure 7B:
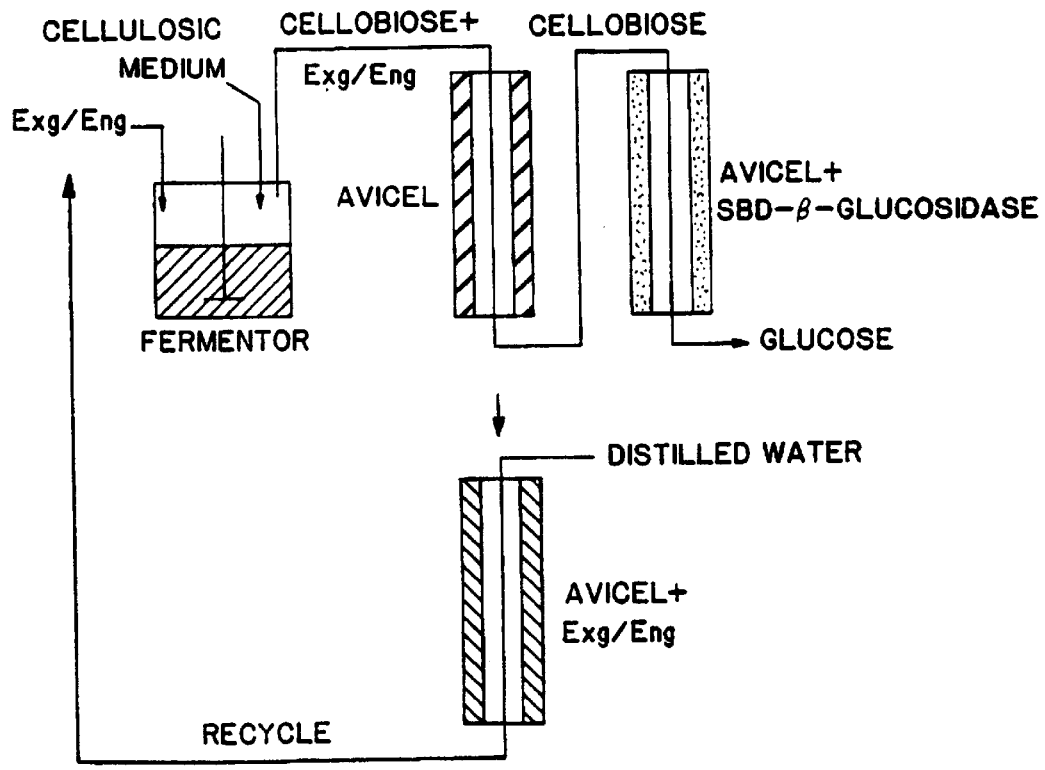

Production of Glucose from Cellobiose Using β-glucosidase Fusion Protein Immobilized on Avicel This procedure uses endoglucanase-exoglucanase coincubation with subsequent channeling of the resulting cellobiose mixture into an Avicel column upon which β-glucosidase is immobilized (See FIG. 7B). The method is as follows. In a fermentation vessel a suitable proportion of both endoglucanase and exoglucanase is added to a medium containing the cellulosic material to be degraded. The enzymes are allowed to react for a fixed period of time to produce cellobiose which is solubilized in the medium. The whole spent medium together with the enzyme is first passed through an Avicel column which immobilizes and concentrates both the endoglucanase and the exoglucanase. The eluent containing the cellobiose is channeled to a second Avicel column with immobilized β-glucosidase $CBD_{Cex}$ fusion protein which then hydrolyses the cellobiose into glucose units The endoglucanase and the exoglucanase are regenerated from the first column by elution. Both columns can be reused several times for purification and enzymatic conversion.

EXAMPLE 6

Preparation of CenA-alkaline Phosphatase Fusion Protein Expression Cassette

TnphoA is a derivative of transposon Tn5 containing the *E. coli* alkaline phosphatase gene, phoA, minus its signal sequence ('phoA). Transpositional insertion into an expressed gene in the correct reading frame creates a PhoA fusion protein. If the target gene contains protein export signals, these can direct the secretion of the fusion protein. This secretion is detectable by alkaline phosphatase activity, which is present only when the enzyme has been secreted to the periplasmic. TnphoA is used to create phoA gene fusions with the *C. fimi* cenA gene in a plasmid having a multiple cloning site. A gene encoding a protein of interest can be cloned into a multiple cloning site (mcs) and expressed as a fusion protein. The gene product is purified by binding to cellulose, such as Avicel, and cleavage from the CenA fusion partner with *C. fimi* protease.

A. Preparation and Analysis of Gene Fusions

Transpositional mutagenesis with TnphoA is used to create gene fusions with cenA. The plasmid containing cenA is pUCEC2, a 1.6 kb SstI cenA fragment cloned in pTZ18U, a multifunctional derivative of pUC18 (Yanisch-Perron et al., *Gene* (1985) 33:103–119). pTZ18U is available from U.S. Biochemicals.

Oligonucleotide-directed mutagenesis (Zoller et al., *Nucleic Acids Res.* (1982) 10:6487–6500 and Zoller et al., *Methods Enzymol.* (1983) 100:468–500) was used to delete the carboxy-terminal portion of the cenA gene and juxtapose the Pro-Thr box and the multiple cloning site of pTZ18U. Screening procedures include dot blot hybridization using the mutagenic oligonucleotide as a probe, and restriction analysis. DNA sequencing by the chain-termination method was performed to verify the sequence of the deletion region (Yanisch-Perron, supra).

The transposition event was mediated by infection of *E. coli* CC118 (pUCEC2) with a defective lambda phage containing the transposon, λTnphoA-1 (Gutierrez et al., *J. Mol. Biol.* (1987) 195:289–297). pUCEC2 (FIG. 4) was derived by transferring the cenA coding sequence from pcEC-2 into the expression vector pUC18 (Guo et al. (1988) FEMS Microbiol. Lett 49, 279–283). *E. coli* CC118 contains a deletion in the phoA gene. Transpositional insertion into the cenA gene in-frame with CenA creates a CenA-PhoA fusion protein which is exported to the periplasm, secretion being promoted by the CenA signal peptide. Colonies selected for kanamycin (transposon-derived) and ampicillin resistance were screened for alkaline phosphatase activity on the chromogenic substrate 5-bromo-4-chloro-3-indolyl phosphate (XP). Plasmid DNA from PhoA+ colonies was retransformed, and selected and screened as above. PhoA+ colonies were screened for endoglucanase activity on carboxymethylcellulose (CMC) plates stained with Congo red (Greenwood et al., FEES Letters (1984) 2:259–263). The desired phenotype is PhoA+, Eng−, and resistance to ampicillin and kanamycin.

Plasmid DNA was isolated from PhoA+, EngA-colonies and analyzed by restriction digestion and agarose gel electrophoresis. Of 55 colonies screened, 34 had TnphoA insertions in cenA in the correct orientation. The insertions occurred throughout the cenA gene. Some of these clones can have out-of-frame insertions, a possibility that becomes evident when looking at the protein products of the fusions. Analysis of cellulose binding of some of the CenA-PhoA fusion proteins shows that the fusion proteins bind to filter paper, despite stringent washes with 50 mM phosphate buffer (pH 7.0) and 0.5 M NaCl.

One fusion protein which binds to cellulose and contains the *C. fimi* protease cleavage site was selected for further study. The exact insertion position of TnphoA was determined by DNA sequencing using the chain-termination method. The buffer conditions which facilitate binding to Avicel and for which elution from Avicel occurs were also determined as described above (see Example 3).

For these fusions which contain a *C. fimi* protease site (PT), for example, CBD-PT-PhoA, the Avicel-bound fusion protein is incubated with *C. fimi* protease, and released proteolytic fragments concentrated by ultrafiltration and analyzed by SDS-PAGE and PhoA activity zymogram or Western immunoblot, or by gel filtration chromatography. Substrate-bound fragments were dissolved in SDS and analyzed by SDS-PAGE and Western immunoblot, probed with antiserum to the Pro-Thr box (Langsford et al., *FEBS Letters* (1987) 225:163–167).

B. Purification of Fusion Protein

Cleared *E. coli* cell extracts containing the fusion protein were applied to an Avicel column in a buffer which promotes binding of the fusion protein to the Avicel matrix (e.g., 50 mM phosphate, pH 7.0). After thorough washing of the column with buffer to remove non-specifically bound proteins, *C. fimi* protease was applied to the column and washed through with buffer. Collected fractions were assayed for alkaline phosphatase activity, and the enzyme peak further purified by ion exchange or gel filtration chromatography. Purification conditions, such as protease concentration and flowrate, were varied to optimize the recovery of alkaline phosphatase activity.

EXAMPLE 7

Use of *Cellulomonas fimi* Cellulose Binding Domains for Drug Delivery

A. Solubility/Persistence Interleukin 2

A fusion protein comprising interleukin 2 (IL2) linked to the cellulose binding region of a *C. fimi* cellulase was prepared as described above by preparing a fusion gene comprising the DNA sequence encoding the CenA cellulose binding region and a gene encoding IL-2 or a functional portion thereof and transforming it into an expression host such as *E. coli*. The Cen CBD-IL2 fusion protein was purified by affinity chromatography on cellulose (Avicel or cotton). The fusion protein then was eluted with 6M guanidyl hydrochloride, then bound to soluble (carboxymethyl) or insoluble (Avicel) cellulose. The conjugate is injected into mice (i.p.) and the kinetics of IL-2 clearance from the peritoneal fluid determined. The soluble conjugate is injected i.v. and the kinetics of clearance of IL-2 activity from the blood determined. The conjugates find use in decreasing the clearance rate of IL-2 from the circulation.

B. Antigenicity/Adjuvant Activity

Two fusion proteins comprising IL-2 and alkaline phosphatase respectively linked to the cellulose binding region of *C. fimi* cellulose, prepared as described above, are bound to the same cellulose preparation through the cellulose binding domain (CBD) on each fusion protein. Both soluble (for example, carboxymethyl) and insoluble (for example, Avicel) cellulose matrices are used. The combined matrix IL2-CBD cellulase- CBD-alkaline phosphatase is injected into mice and the immune responses (T-cell proliferation and anti-alkaline phosphatase antibody concentration) determined after 1 week and 2 weeks. These responses are compared to the response generated by injecting an identical amount of alkaline phosphatase-CBD. In subsequent experiments HIV gp 120-CBR and Pseudomonas porin-CBR are tested in an analogous system replacing alkaline phosphatase. The combination of IL-2 in close proximity to an antigen finds use in enhancing the immune response to the presented antigen.

EXAMPLE 8

Production of CBD-Coomassie Blue and CBD-Fluorescein or Rhodamine Isothiocyanate (CBD-FITC or CBD-TRITC)

CBD-conjugates were created by attaching either Coomassie blue R 250™ or FITC to expressed and isolated CBDs.

Figure 8:
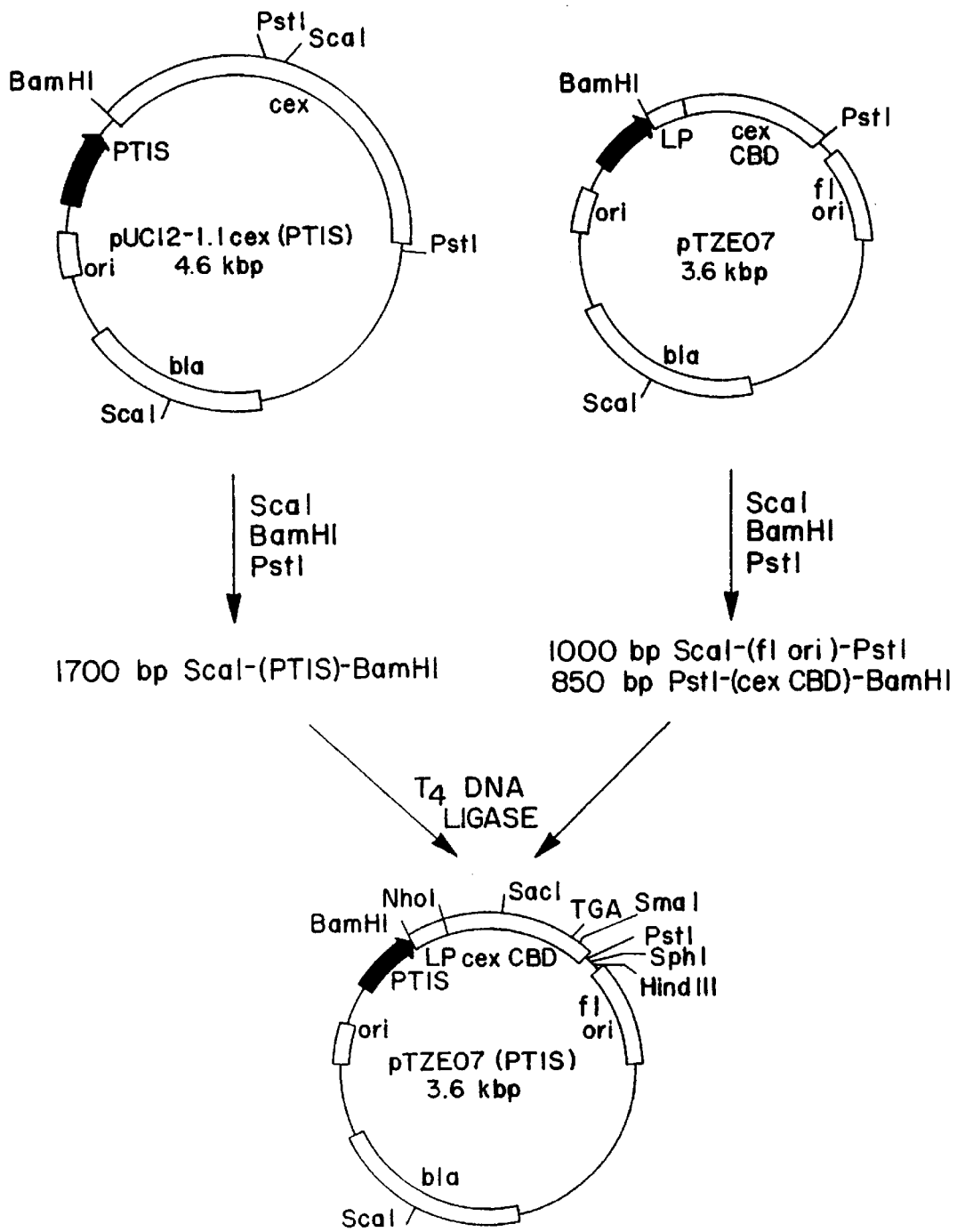
FIG. 8 shows construction of pTZEO7 (PTIS). pUC12-1.1cex (PTIS) was completely digested with ScaI, BamHI and PstI and the 1.7 kbp fragment containing the PTIS sequence was isolated. pTZEO7 was digested completely with ScaI, BamHI and PstI and the 1 kbp and 0.85 kbp fragments were isolated. The 1.7, 1 and 0.85 kbp fragments were ligated to give pTZEO7 (PTIS).

CBD Cex was expressed from the PTZE07 (PTIS) vector (see FIG. 8) containing an insert from a fragment, encoding 110 amino acids from *C. fimi* cellulase (CBDcex). The CBDcex DNA insert corresponds to the Cex CBD gene fragment discussed above in Example 3. The expression product of the fragment, an 8 kD protein as determined by PAGE, was isolated on Avicel (microcrystalline cellulose) columns as indicated in Table 1 below. The isolated CBD was stored until attached to a dye or fluorescent label as described below.

Coomassie blue R 250 from BioRad™ was attached to CBDcex by incubating CDBcex with 2% Coomassie blue in 50 mM KPO4 buffer, pH 7 for minutes at 20° C. to yield CBDcex-Coomassie. FITC or TRITC was attached to the CBDcex as follows. Both fluorescein and rhodamine isothiocyanate derivatives can be used for coupling reactions. The major problem encountered is either over- or undercoupling, but the level of conjugation can be determined by simple absorbance readings (see below).

TABLE 1

PURIFICATION OF CBDCex FROM CULTURE SUPERNATANT

| | | |
|---|---|---|
| 1. | Culture Volume: | 60 L in LB + ampicillin (100 μg.ML$^{-1}$) + IPTG (0.1 mM) |
| 2. | Cellulose: | 1.08 kg of Avicel PH-101 (dried powder) |
| 3. | Binding conditions: | Overnight; room temp; periodic manual stir |
| 4. | Avicel washes: (per 30 L) | 4 × 1 L 1M NaCl in 50 mM phosphate, buffer, pH7 |
| 5. | Desorption (per 30 L): | 2 extractions: 2 × 1 L 8M GdmCl in 50 mM phosphate buffer, pH7 |
| 6. | Ultrafiltration through YM-2 membrane (Amicon) and exchange with water. | |
| 7. | Results: Total mount of recovered CBD$_{Cex}$: | 320 mg (1st extraction) 950 mg (2nd extraction) |
| | approx. | 1200 mg total |
| | Adsorption load: | 1.11 μg CBD$_{Cex}$.mg Avicel$^{-1}$. |
| | Yield: | 20 mg CBD$_{Cex.L}$ culture supernatant$^{-1}$. |
| | Productivity: | 1 mg CBDBD$_{Cex}$.L culture supernatant$^{-1}$.h-. |

Prior to the coupling, a gel filtration column is prepared to separate the labeled CBD from the free fluorochrome after the completion of the reaction. A gel matrix with an exclusion limit of 10,000 for globular proteins is used (eg Sephadex G25). Fine-sized beads (approximately 50 μm in diameter) are preferred.

The column that is needed is determined by multiplying the total volume of the reaction by 20. Prepare a column of this size according to the manufacturer's instructions (swelling, etc.) and the column is equilibrated in PBS.

A CBD solution of a least 1 mg/ml in 0.1 M sodium carbonate (ph 9.0) is prepared. The fluorescein isothiocyanate (FITC) or tetramethyl-rhodamine isothiocyanate (TRITC) is dissolved in dimethyl sulfoxide (best grade available, with no water) at 1 mg/ml. The solution is prepared fresh for each labeling reaction. For each 1 ml of protein solution, 50 μl of the dye solution is added. The dye should be added very slowly in 5-μl aliquots, and the protein solution should be gently but continuously stirred during the addition. The reaction is then left in the dark for 8 hours at 4° C. NH$_4$Cl to 50 mM is then added and the mixture incubated for 2 hr at 4° C. Xylene cylanol to 0.1% and glycerol to 5% are then added. The unbound dye is separated from the conjugate by gel filtration and the coupling reaction carefully layered on top of the column. The conjugated CBD is then eluted with PBS. It can usually be seen under room light. The conjugate is stored at 4° C. in the column buffer in a lightproof container. If appropriate, sodium azide to 0.02% is added. When using low concentrations of CBD (i.e., <1 mg/ml), normally it is advantageous to add BSA to a final concentration of 1%.

For fluorescein coupling, the ratio of fluorescein to protein can be estimated by measuring the absorbance at 495 nm and 280 nm. For rhodamine, it is measured at 575 nm and 280 nm. For rhodamine, it measured at 575 nm and 280 nm. The ratio of absorbance for fluorescein (495–280 nm) is between 0.3 and 0.7. Ratios below these yield low signals, while higher ratios show high backgrounds. If the ratios are too low the conjugation can be repeated using lower levels of CBD and higher levels of dye. If higher levels are found, the labeling can be repeated with appropriate changes or the labeled CBD can be purified further by FPLC column chromatography.

EXAMPLE 9

Use of CBD-Coomassie and CBD-Fluorescein Isothiocyanate (CBD-FITC)as Removable Inks A. For paper The selective binding and removal of CBDcex-Coomassie blue from paper was tested by comparing the amount of dye selectively bound to the paper when the dye was attached to Bovine Serum Albumin (BSA), attached to PBDcex or free in solution. Two types of paper were used, Whatman's #3 and Nitrocellulose. CBDcex Coomassie blue was placed on either paper in circles, dried for 2 minutes and washed in 250ml of K$_3$PO4 buffer pH 7 for 15 hours, 500ml of K$_2$PO4 buffer pH 7 for 5 hours and 200 ml of K$_2$PO4 buffer, pH 7 for 1 hour. Nonspecifically bound dye was removed by destaining in 5% Acetic Acid in 10% methanol overnight to 24 hours. The papers were then oven dried for 15 minutes at 50° C. Following the wash steps, free dye does not bind and dye bound to BSA binds weakly, whereas CBDcex-Coomassie blue remains bound to the paper.

The CDBcex-Coomassie blue was removed from paper with a solution of low ionic strength (for example, distilled waters) or high pH (for example, sodium carbonate buffer, pH9, or 0.1 M NaOH). The CDBcex-Coomassie blue also was removed from paper by treatment with protease K (50 μg/ml, 37° C., 20 min.).

B. For clear packaging material

The selective binding and removal of CBDcex-Coomassie was tested on reconstituted cellophane packaging material.

C. For living plant tissue

The selective binding and removal of CBDcex-FITC was demonstrated on living plant tissue (e.g., spruce needles).

D. For cotton fibers

The selective binding and removal of CBDcex-FITC was tested on cotton fibers. CBDcex was bound to the fibers in buffer for 10 minutes. The fibers were washed five with 50 mM phosphate buffer, pH 7.0. No CBDcex-FITC was removed from the fibers after the first two washing steps. However, the CBDcex-FITC was removed completely in the presence of protease K (50 mg/ml, 370, 20 min.).

EXAMPLE 10

Purification of CenA,p30 and CBD.PT$_{CenA}$.

Figure 9:
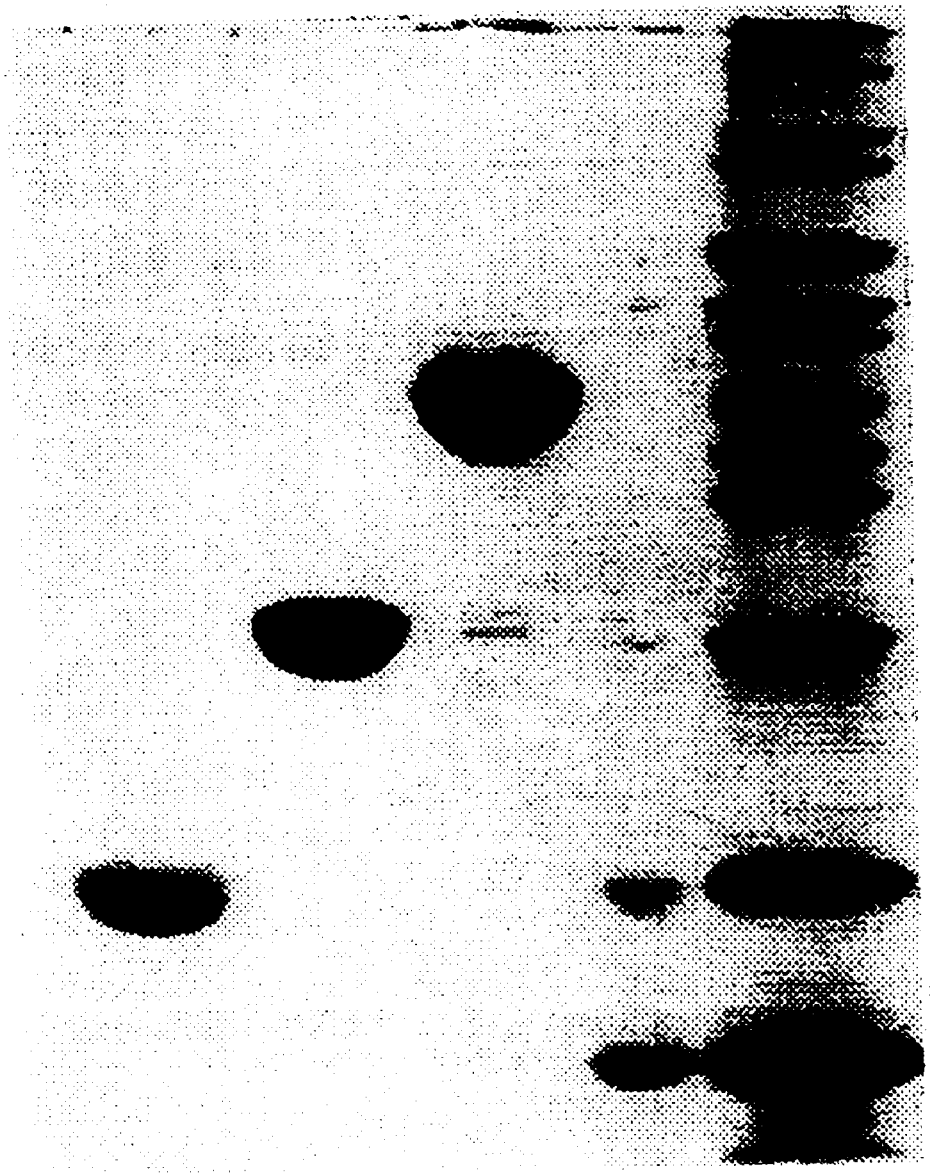
FIG. 9 shows SDS-PAGE analysis of CBD.PT CenA, p30 and CenA. Purified CBD.PT$_{CenA}$ (lane 1), p30 (lane 2) and CenA (lane 3) were analyzed on a gel containing 12.5% acrylamide. Each lane was loaded with 10 g protein. Arrowheads on the right indicate the positions of the molecular mass standards (212, 130, 116, 97.4, 68, 53, 45, 41, 36, 29, 20 and 12.4 kDa; from the top of the figure) shown in lane 4.
Figure 11:
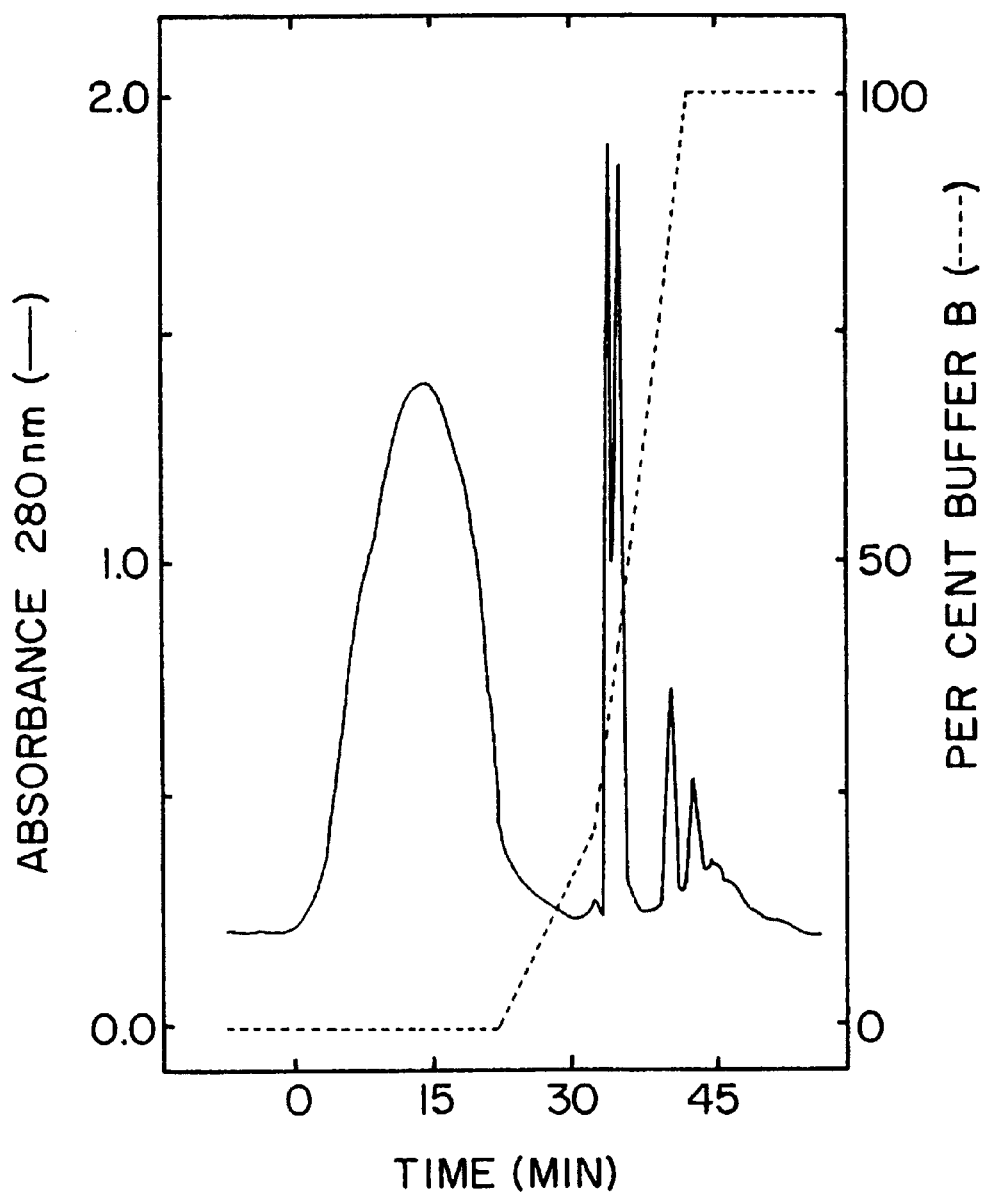
FIG. 11 shows anion-exchange chromatography of CBD.PT$_{CenA}$. Partially purified CBD.PT (10 mg in 10 ml 2 μM NH$_4$OH, pH 9.4) was loaded onto an anion-exchange column at 0 min and chromatographed as using a Mono Q column equilibrated with 2 mM NH$_4$OH, pH 9.4, operated at a flow rate of 1.0 ml/min. The partially purified protein was chromatographed in 10 mg aliquots. CBD.PT$_{CenA}$ was recovered in the column flow-through; contaminating proteins remained bound to the column and were removed with a salt gradient (0.0–0.5 M Na acetate, pH 9.8).

Purification of the non-glycosylated form of CenA, synthesized from recombinant C. fimi DNA in E. coli (FIG. 9, lane 3), has been described Gilkes et al. (1988) J. Biol. Chem., 263:10401–10407. This enzyme is cleaved by a C. fimi protease between Thr 165 and Val 166 (i.e. at the carboxyl terminus of the P.T. box) into two fragments. The stable, 29.7 kDa, carboxyl-terminal fragment (p30) comprises the CenA catalytic domain; this can be purified from the digest by size-exclusion chromatography (FIG. 9, lane 2). The corresponding amino-terminal fragment, which comprises the CBD plus the P.T box, is produced in non-stoichiometric proportions, presumably because it is susceptible to further proteolysis Gilkes et al. above. Therefore, an alternative method for the production of this polypeptide was adopted. The cenA gene was manipulated in vitro to remove the region encoding the catalytic domain (FIG. 10A). The resulting gene fragment was ligated into pUC18 to give the recombinant plasmid pUC18-CBD.PT (FIG. 10B) which was used to transform E. coli. The cenA gene fragment on this plasmid encodes the protein CBD.PT$_{CenA}$ (i.e. the entire CBD, plus the P.T box lacking Thr 165), as shown in FIG. 10C. CBD.PT$_{CenA}$ was purified from an E.

coli JM101 (pUC18CBD.PT) cell extract by cellulose affinity chromatography as in Gilkes et al. above and anion-exchange chromatography (FIG. 11). CBD.PT$_{CenA}$ bound very weakly to the anion-exchange column at pH 9.4 (i.e. 3.2 pH units above its theoretical pI), presumably because of its low charge density (Warren et al. (1986) Proteins, 1:335–341). However, since contaminating proteins were more strongly bound, the chromatographic step was effective. The purified CBD.PT$_{CenA}$ preparation was homogeneous, as judged by SDS-PAGE (FIG. 9, lane 1). Its apparent molecular mass (20.0 kDa), relative to standard proteins, was greater than the molecular mass predicted from its primary structure (14.1 kDa). The PT box was previously shown to cause anomalous electrophoretic migration (Gilkes et al. (1989) J. Biol. Chem., 264:17802–17808). p30 was also purified to apparent homogeneity (FIG. 9, lane 2); a minor ($\leq$1% total) 30 kDa contaminant was evident in the purified CenA preparation (FIG. 9, lane 3).

EXAMPLE 11

Analysis of the adsorption of CenA, CBD.PT$_{CenA}$ and p30 to BMCC

Figure 12A:
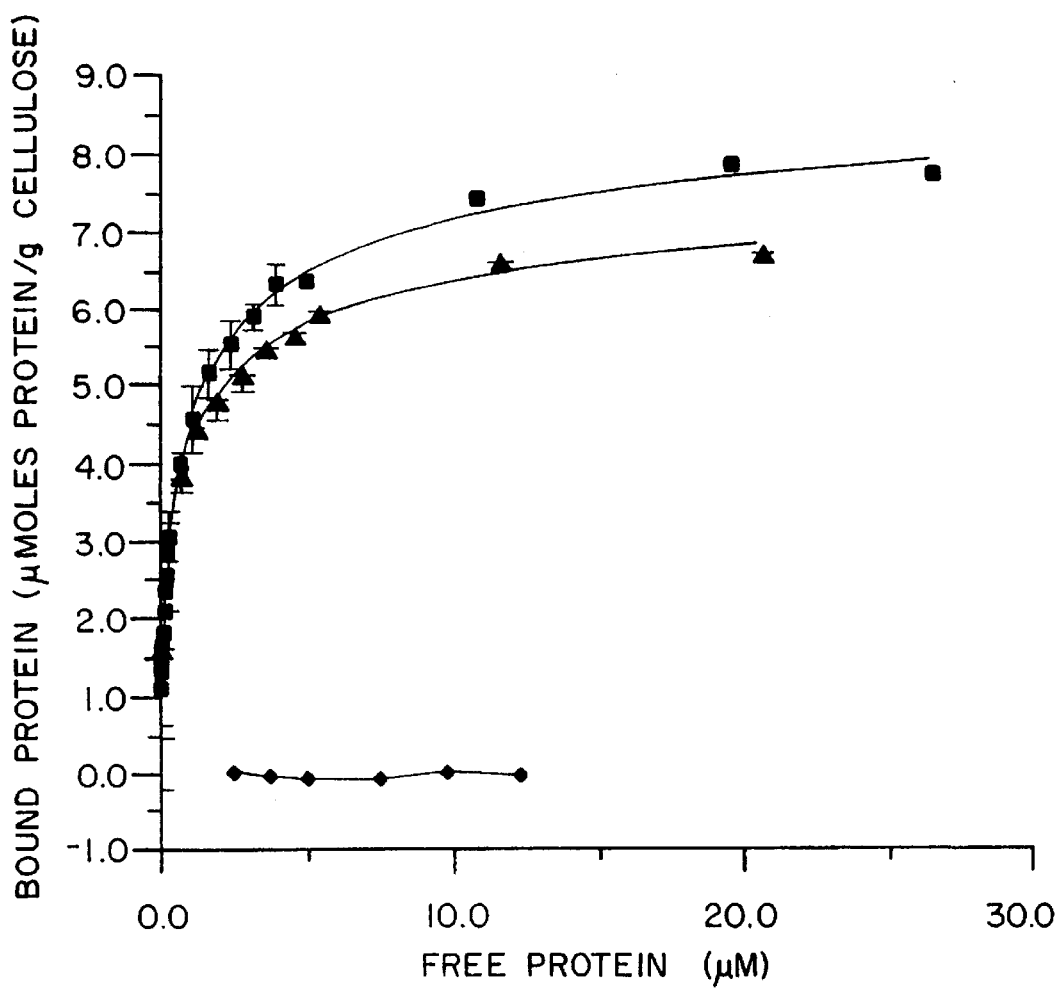
FIGS. 12A and 12B show adsorption of CenA and its isolated domains to Bacterial microcrystalline cellulose (BMCC).
Figure 12B:
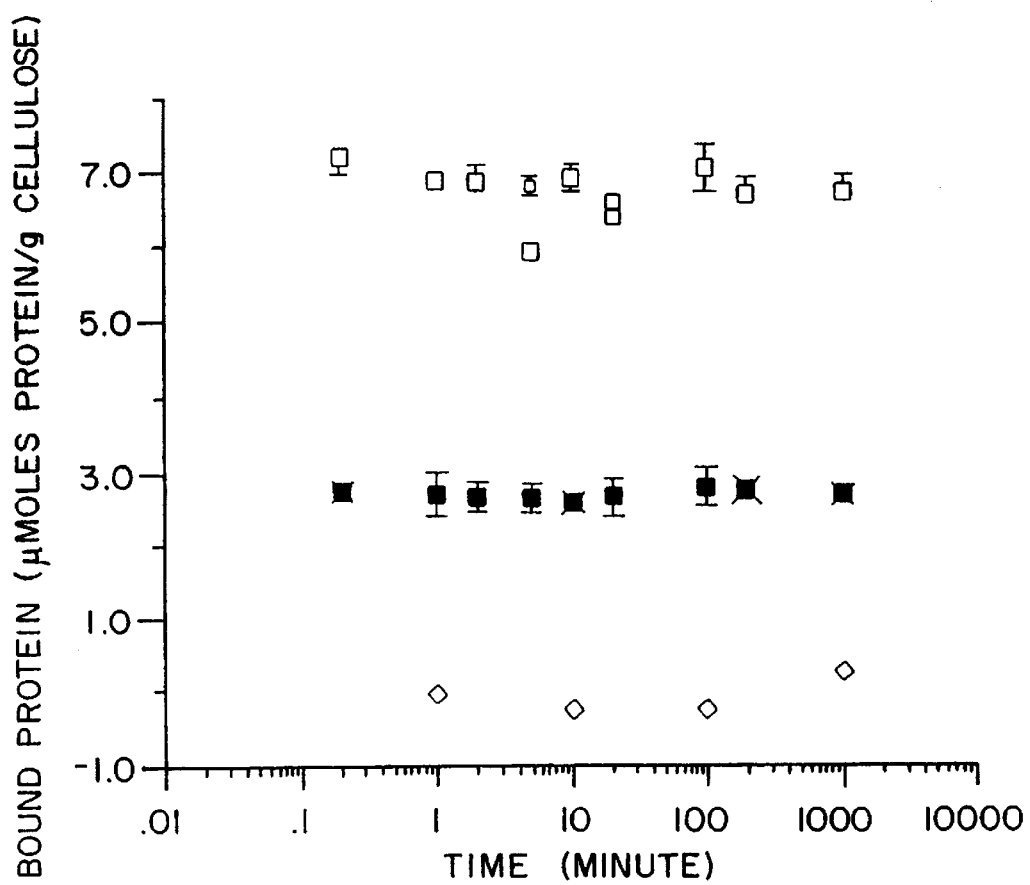

The kinetics of the adsorption of CenA and CBD.PT$_{CenA}$ to bacterial microcrystalline cellulose (BMCC) at 30° C. are shown in FIG. 12 (inset). High and low total protein concentrations, relative to the concentration range used to measure adsorption isotherms, were tested. Equilibration was complete within the shortest experimentally feasible incubation time (0.2 min), at both concentrations. There was no net desorption of either protein during the following 16.7 h. There was no detectable adsorption of p30. Hydrolysis of BMCC after 18 h incubation with 18.3 $\mu$M CenA amounted to 2.7% of the total cellulose, as determined by the release of soluble reducing sugar; 0.8% hydrolysis was obtained with 18.3 $\mu$M p30. No hydrolysis was detected with CBD.PT$_{CenA}$ at the same molar concentration.

Figure 13A:
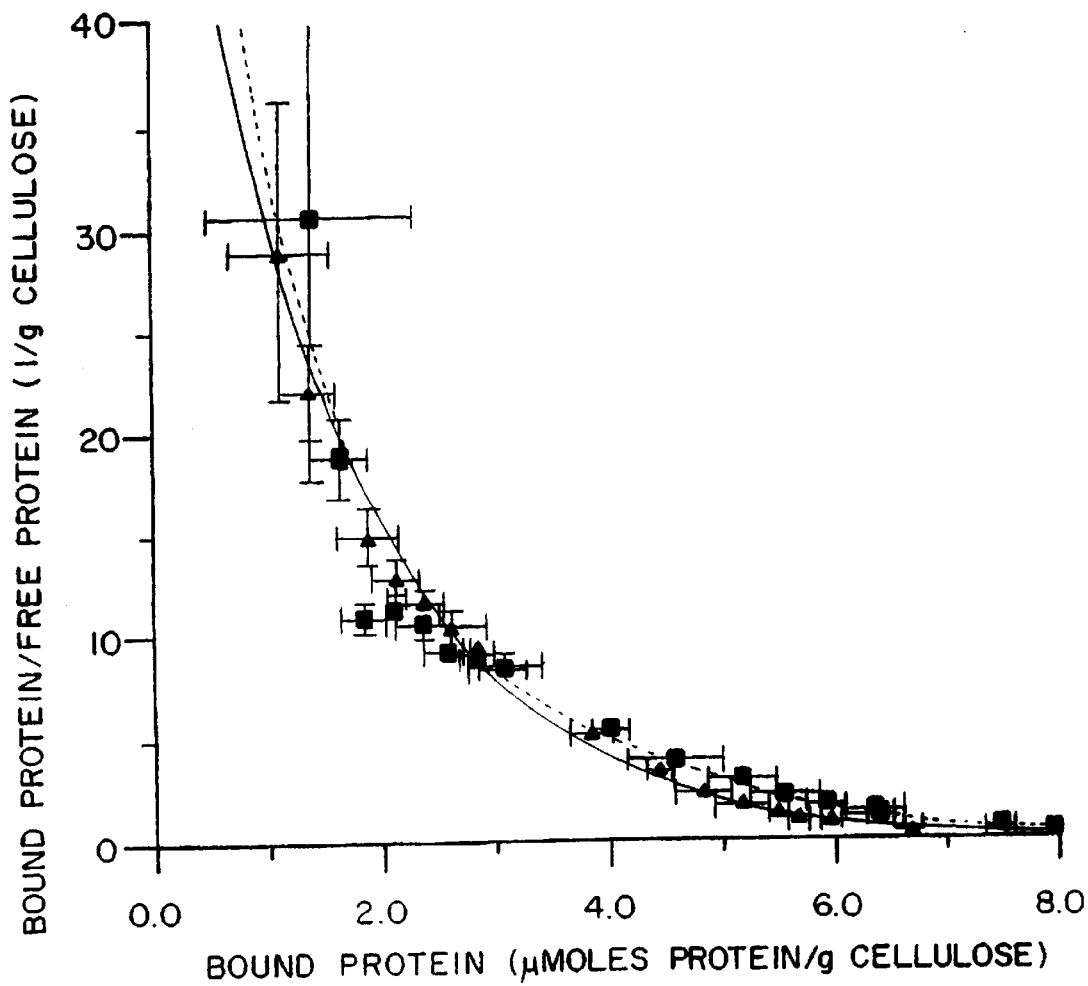
FIGS. 13A and 13B show analyses of the adsorption of CenA and CBD.PT$_{CenA}$ to BMCC. Insert a shows a semi-logarithmic plot ([B] vs. log [F]) of the adsorption data for CenA (open diamond) and CBD.PT$_{CenA}$ (solid square) from FIG. 4.
Figure 13B:
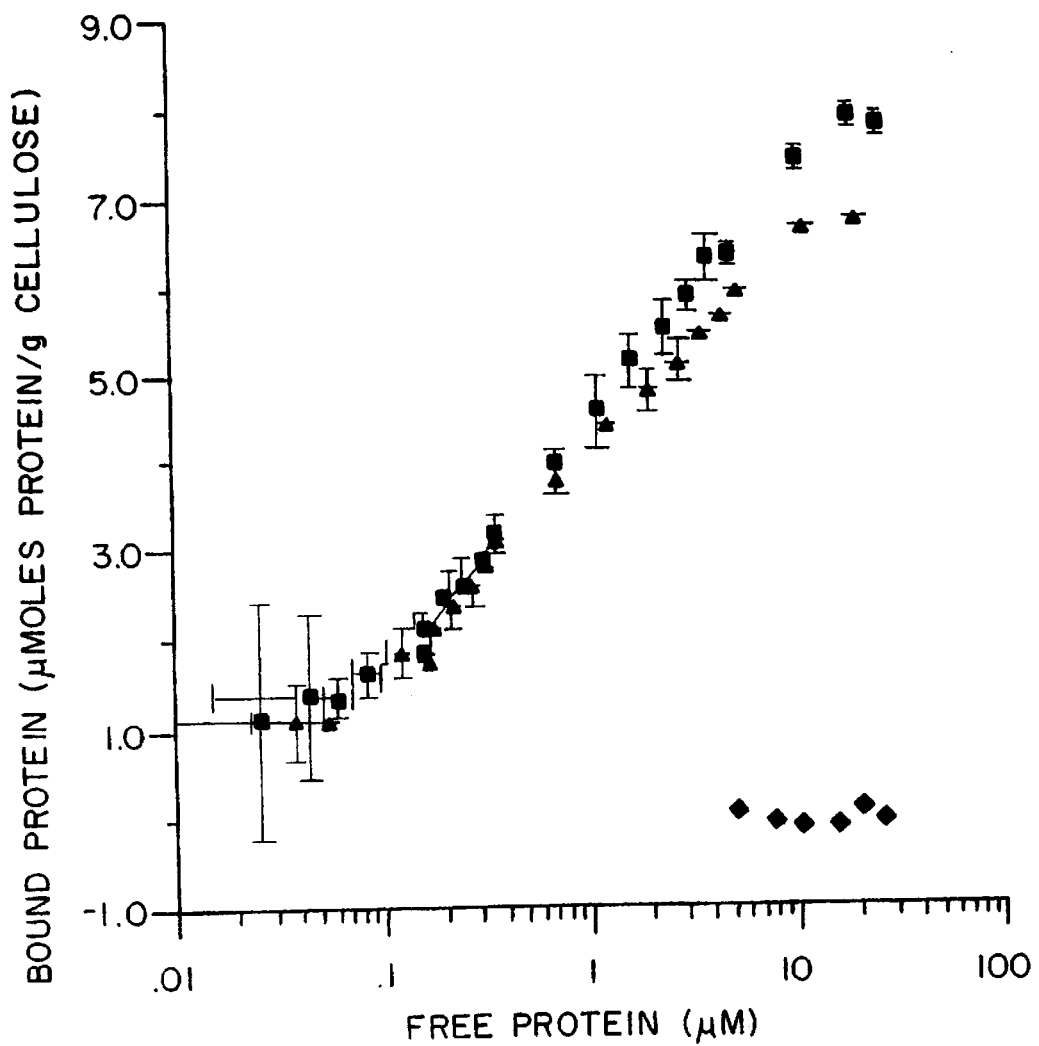

The equilibrium adsorption isotherms for CenA, CBD.PT$_{CenA}$ and p30 (1.1–32.2 $\mu$M total protein) are shown in FIG. 12A. The absence of p30 adsorption found in the kinetic experiment was confirmed. Saturation of BMCC by CenA and CBD.PT$_{CenA}$ was approached but not attained at the highest total protein concentrations used. This failure to reach saturation was emphasized when the same data was plotted in semi-logarithmic form (B vs. log F), as shown in FIG. 13B. Scatchard plots of the data for CenA and CBD.PT$_{CenA}$ (FIG. 13A) were non-linear (concave upward), indicating a complex interaction of these proteins with BMCC. The absorption parameters for binding of CenA, CBD.PTCenA and Cex to BMCC are shown in the following Table.

TABLE 2

Absorption parameters for the binding of CenA, CBD.PTCenA and Cex to BMCC

| Ligand | Kr<br>1.g$^{-1}$ | Ka<br>1.mmo$^{-1}$ | a/[N$_o$]<br>g.mmol$^{-1}$ | a<br>mol.mol$^{-1}$ |
|---|---|---|---|---|
| CenA | 40.5;3.3 | 0.401;0.032 | 0.325;0.014 | 32.9;1.4 |
| CBD.PTCenA | 45.3;2.1 | 0.449;0.020 | 0.357;0.002 | 39.2;0.2 |
| Cex | 33.3;5.5 | 0.330;0.051 | 0.276;0.113 | 27.9;11.4 |

Figure 14A:
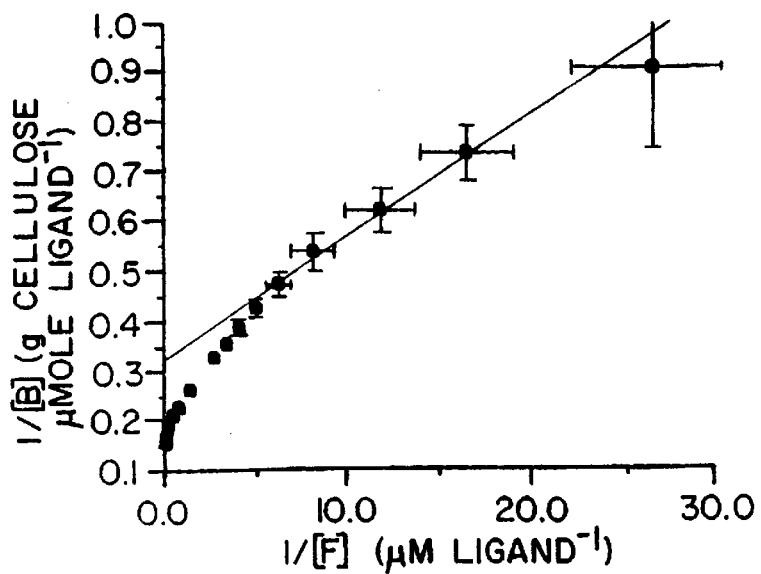
FIGS. 14A–14C show double reciprocal plots of adsorption data for CenA and CBD.PT$_{CenA}$ and Cex. The adsorption data for CenA and CBD.PT$_{CenA}$ from FIG. 4 are shown in 14A and 14B, respectively; data for Cex are shown in 14C. Data are plotted in double reciprocal form (1/[B] vs. 1/[F]), with standard errors in both dimensions indicated by vertical and horizontal bars. The $K_r$ and a/[$N_O$] values listed in Table 2 were estimated from the limiting slopes (straight lines) of these plots and their intercepts on the 1/[B] axis, respectively, according to equations (6) and (7) as outlined in Example 3, C. In each case, the slope was obtained by fitting lines through data points for the five lowest values of [B].
Figure 14B:
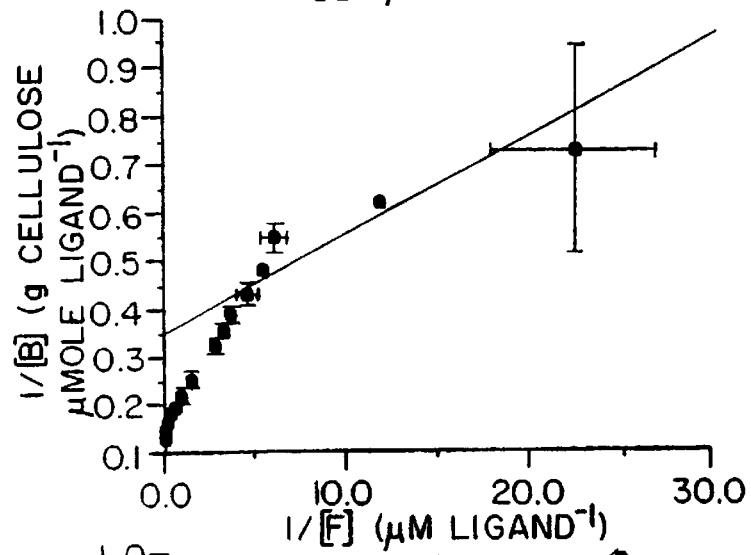
Figure 14C:
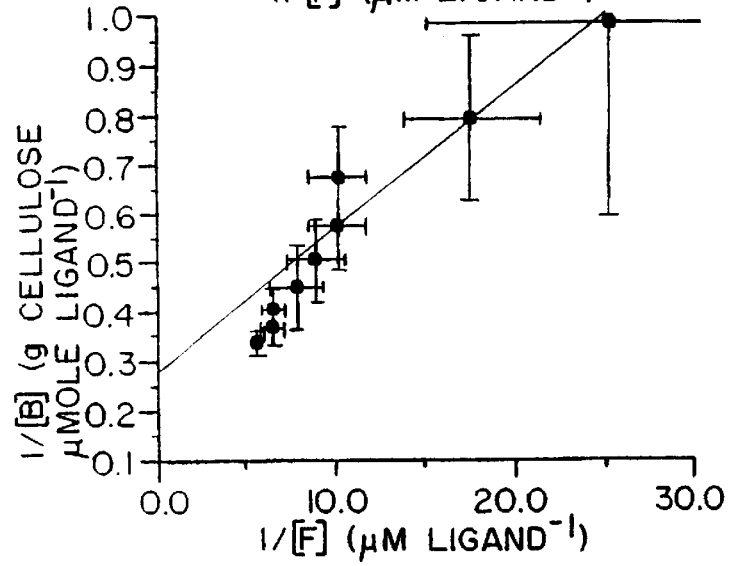

The parameters ($\pm$ accumulated standard error) were calculated from adsorption data plotted in double reciprocal form (FIGS. 14A–14C), as described in Example 3, C. The values for K$_a$ and a were calculated using [No]=101 $\mu$mol lattice residues.g cellulose$^{-1}$, as detailed in Example 3, C. Adsorption and relative affinity of CBD$_{Cex}$ to cellulose, including Avicel, BMCC and regenerated cellulose (RC), and of chitin are shown in FIGS. 15A–15E and 16A–16E.

Figure 17A:
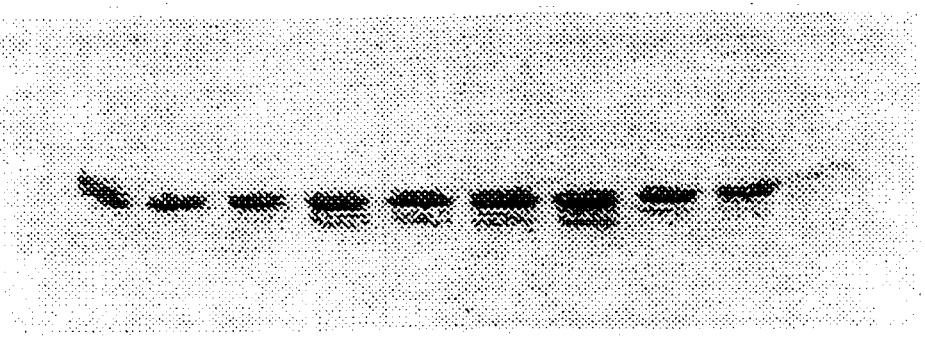
FIGS. 17A–17C show the influence of detergents on the binding of CBD$_{cex}$ to cellulose. The percentage of gel used was 16%T. Protein loading per lane was approximately 1.8 nmoles. The detergent was added either after binding of CBDcex to cellulose (17A, open lanes) or present during binding of CBDcex to cellulose (17B, cross-hatched lanes). FIG. C shows a densitometric scan of protein bands. Lanes 1–5, CBDcex treated with Triton X-100 (0, 0.002%, 0.02%, 0.2% and 2%, respectively). Lanes 6–10, CBDcex treated with SDS (0, 0.002%, 0.02%, 0.2% and 2% respectively).
Figure 17B:
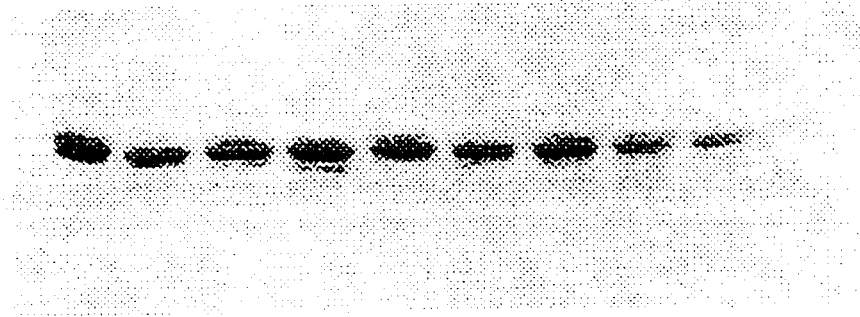
Figure 17C:
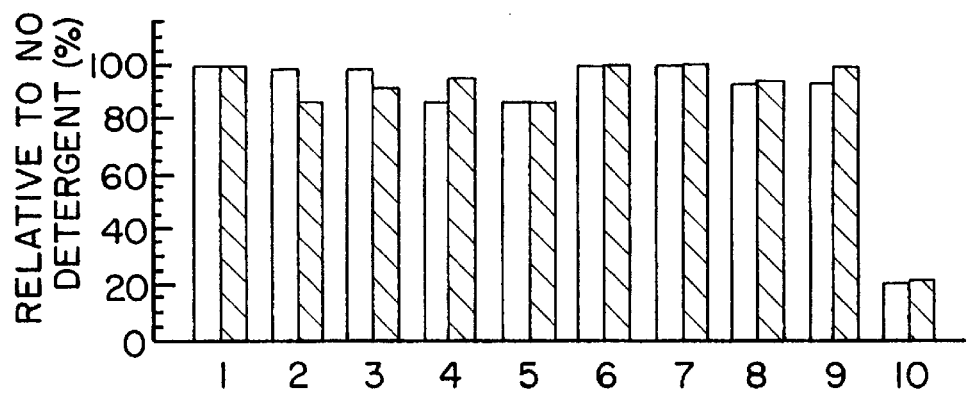
Figure 18:
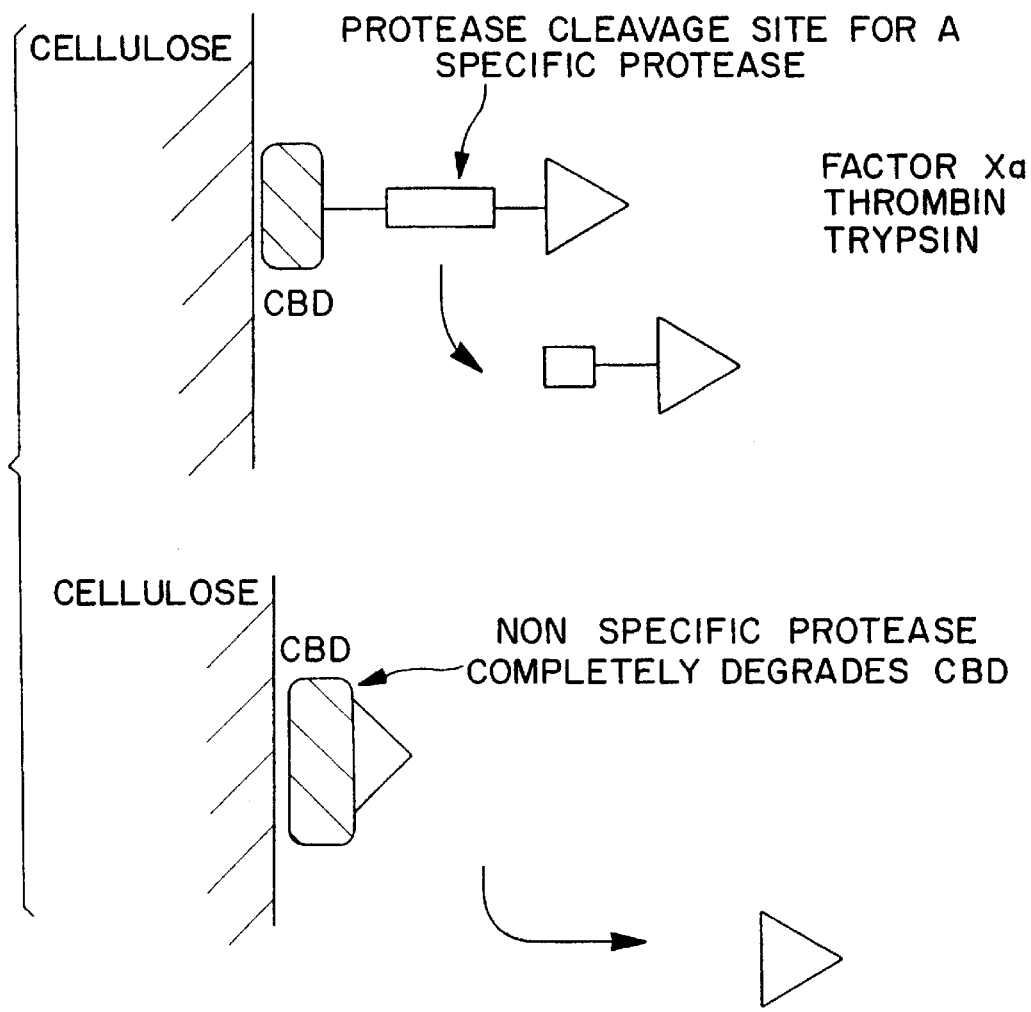
FIG. 18 shows two removable label compositions and means for enzymatically debinding the removable label from a cellulose substrate, where an arrow indicates a chemical moiety, an open box indicates a protease cleavage site for a specific protease, and a cross-hatched box indicate a cellulose binding domain.

FIGS. 17A–17C show the influence of adding detergents on the binding of CEB$_{Cex}$ to the compositions of the subject invention comprise hybrid proteins in which at least the polysaccharide binding domain of a polysaccharidase is coupled to a ligand of interest such as a protein or a chemical moiety, for example a dye or pigment. Examples of enzymatically debinding two different removable label compositions from cellulose are shown in Example 18.

The compositions find use for binding a variety of ligands to a polysaccharide matrix such as cellulose or chitin or one of their chemical derivatives, either soluble or insoluble. The compositions can be used bound to the matrix, for example as drug delivery systems, or in bioreactors and immobilized enzyme reactors or they can be used as a means of isolating or purifying the ligand, then recovering the ligand following cleavage with a specific protease. They also find use in reversibly binding a dye, such as ink or a fluorescent compound such as fluorescein or rhodamine to a polysaccharide matrix such as paper or cotton.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A composition comprising:
   as components (1) a conjugate comprising (a) a non-protein chemical moiety selected from the group consisting of a tag, an antibiotic, a fungicide, an insecticide and a texturing agent joined to (b) a non-fusion polypeptide having an amino acid sequence comprising a substrate binding region of a cellulase which binds to a β-1,4-glycan substrate, wherein said polypeptide is derived from a cellulase and said polypeptide is essentially lacking in hydrolytic activity of said cellulase; and (2) a β-1,4-glycan substrate for said cellulase wherein component (1) is bound to component (2) via (b).

2. The composition according to claim 1, wherein said β-1,4-glycan substrate comprises an insoluble cellulose or chitin.

3. The composition according to claim 2, wherein said insoluble cellulose is from a source selected from the group consisting of microcrystalline cellulose, cotton and a lignocellulosic material.

4. The composition according to claim 1, obtained by the method of contacting said conjugate with a β-1,4-glycan substrate region binds to said β-1,4-glycan substrate.

5. The composition according to claim 1, wherein said chemical moiety is a radionuclide.

6. The composition according to claim 1 wherein said tag is a chromophore.

7. The composition according to claim 6, wherein said chromophore is selected from the group consisting of:

(a) fluorescein isothiocyanate; and
   (b) tetramethyl rhodamine isothiocyanate.

8. The composition according to claim 1, wherein said tag is dye.

9. The composition according to claim 8, wherein said dye comprises Coomassie blue.

10. The composition according to claim 1, wherein said β-1,4-glycan substrate is paper.

11. The composition according to claim 3, wherein the source of said lignocellulosic material is wood.

12. The composition according to claim 1, wherein said β-1,4-glycan substrate is soluble.

13. The composition according to claim 12, wherein said β-1,4-glycan substrate comprises carboxymethyl cellulose.

14. The composition according to claim 1, wherein said tag is a pigment.

15. The composition according to claim 1, wherein said tag is a fluorescor.

16. The composition according to claim 3, wherein the source of said lignocellulosic material is wood pulp.

17. The composition according to claim 3, wherein the source of said lignocellulosic material is a plant tissue.

18. The composition according to claim 1, wherein said tag comprises an enzyme co-factor.

19. The composition according to claim 1, wherein said tag comprises an enzyme co-factor.

20. The composition according to claim 1, wherein said non-protein chemical moiety is joined to one or more terminal amine groups of said polypeptide.

21. The composition according to claim 1, wherein said non-protein chemical moiety is joined to one or more sulfhydryl groups of said amino acid sequence.

22. The composition according to claim 1, wherein said chemical moiety and said polypeptide are conjugated by a hetero bifunctional group.

23. The composition according to claim 1, wherein said chemical moiety and said polypeptide are conjugated by glutaraldehyde.

24. A composition comprising as components (a) a non-protein chemical joined to (b) a non-fusion polypeptide comprising an amino acid sequence comprising a cellulose binding derived from a cellulase, wherein said amino acid sequence binds to a β-1,4-glycan substrate and said polypeptide is essentially lacking in hydrolytic activity of said cellulase.

25. A composition according to claim 23, further comprising as component (c) said β-1,4-glycan substrate bound to said polypeptide.

26. The composition according to claim 25, wherein said amino acid sequence comprises a protease recognition sequence.

27. The composition according to claim 26, wherein said protease recognition sequence is native to said cellulase.

28. The composition according to claim 26, wherein said protease recognition sequence is heterologous to said cellulase.

29. The composition according to claim 25, wherein said components (a) and (b) can be removed from said β-1,4-glycan substrate by a method comprising:

contacting said β-1,4-glycan substrate by a method comprising:

contacting said β-1,4-glycan substrate containing components (a) and (b) with a removal solution having a characteristic selected from the group consisting or low ionic strength and high pH.

30. The composition according to claim 26, wherein said components (a) and (b) can be removed from component (c) by a method comprising:

contacting said β-1,4-glycan substrate with a removal solution comprising a protease which cleaves said amino acid sequence at said protease recognition sequence.

31. The composition according to claim 30, wherein said protease is a non-specific protease.

32. The composition according to claim 25, further comprising a specific protease cleavage site between said non-protein chemical moiety and said amino acid sequence.

33. The composition according to claim 32, wherein said specific protease cleavage site is for a protease selected from the group consisting of:

(a) Factor $X_a$;

(b) Thrombin; and (c) Trypsin.

34. The composition according to claim 24, wherein said non-protein chemical label is selected from the group consisting of a chromophore, a dye, a pigment, a fluorescor, and a cofactor.

35. The composition according to claim 34, wherein said cellulose binding domain is from a *Cellulomonas fimi* cellulase.

36. The composition according to claim 35, wherein said cellulase is an endoglucanase (E.C.3.2.1.4) or a cellobiohydrolase (E.C.3.2.19).

37. A composition comprising a non-fusion polypeptide having an amino acid sequence comprising a substrate binding region derived from a *Cellulomonas fimi* cellulase conjugated to Coomassie Blue or fluorescein isothiocyanate, wherein said polypeptide is essentially lacking in hydrolytic activity of said cellulase.

38. A composition prepared by the method of contacting a cellulose with the composition according to claim 37.

39. The composition according to claim 38, wherein said cellulose is cotton or paper.

40. A modified surface comprising a plurality of conjugates bound to a surface of a solid support, wherein a conjugate comprises as components (a) a non-protein chemical moiety selected from the group consisting of a tag, an antibiotic, a fungicide, and insecticide and texturizing agent joined to (b) a non-fusion polypeptide having an amino acid sequence comprising a substrate binding region of a cellulase which binds to a β-1,4glycan substrate wherein said polypeptide is essentially lacking in hydrolytic activity of said cellulase, and wherein said solid support comprises a substrate for said cellulase.

41. The modified surface according to claim 40, wherein said solid support is selected from the group consisting of paper, cloth, and wood.

42. The surface according to claim 40, wherein said tag is a chromophore.

43. A composition comprising a conjugate of non-protein chemical moiety and a non-fusion polypeptide essentially lacking in hydrolytic activity of a cellulase, wherein said polypeptide comprises an amino acid sequence comprising a substrate binding region of a cellulase which binds to a β-1,4-glycan substrate, and wherein said polypeptide is derived from a cellulase.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 109 amino acids
      (B) TYPE: amino acid
      (C) STRANDEDNESS: Not Relevant
      (D) TOPOLOGY: linear (ii) MOLECULE TYPE: peptide (xi) SEQUENCE DESCRIPTION: SEQ ID NO:1:

```
Ala Pro Gly Cys Arg Val Asp Tyr Ala Val Thr Asn Gln Trp Pro Gly
 1               5                  10                  15

Gly Phe Gly Ala Asn Val Thr Ile Thr Asn Leu Gly Asp Pro Val Ser
                20                  25                  30

Ser Trp Lys Leu Asp Trp Thr Tyr Thr Ala Gly Gln Arg Ile Gln Gln
            35                  40                  45

Leu Trp Asn Gly Thr Ala Ser Thr Asn Gly Gln Val Ser Val Thr
50                       55                  60

Ser Leu Pro Trp Asn Gly Ser Ile Pro Thr Gly Thr Ala Ser Phe
65                   70                  75                  80

Gly Phe Asn Gly Ser Trp Ala Gly Ser Asn Pro Thr Pro Ala Ser Phe
                 85                  90                  95

Ser Leu Asn Gly Thr Thr Cys Thr Gly Thr Val Pro Thr
                100                 105
```

(2) INFORMATION FOR SEQ ID NO:2:

(i) SEQUENCE CHARACTERISTICS:
        (A) LENGTH: 108 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:2:

```
Ser Gly Pro Ala Gly Cys Gln Val Leu Trp Gly Val Asn Gln Trp Asn
 1               5                  10                  15

Thr Gly Phe Thr Ala Asn Val Thr Val Lys Asn Thr Ser Ser Ala Pro
                20                  25                  30

Val Asp Gly Trp Thr Leu Thr Phe Ser Phe Pro Ser Gly Gln Gln Val
            35                  40                  45

Thr Gln Ala Trp Ser Ser Thr Val Thr Gln Ser Gly Ser Ala Val Thr
50                  55                  60

Val Arg Asn Ala Pro Trp Asn Gly Ser Ile Pro Ala Gly Gly Thr Ala
65                  70                  75                  80

Gln Phe Gly Phe Asn Gly Ser His Thr Gly Thr Asn Ala Ala Pro Thr
                85                  90                  95

Ala Phe Ser Leu Asn Gly Thr Pro Cys Thr Val Gly
                100                 105
```

(2) INFORMATION FOR SEQ ID NO:3:

(i) SEQUENCE CHARACTERISTICS:
        (A) LENGTH: 104 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:3:

```
Gln Pro Pro Ala Gly Arg Ala Cys Glu Ala Thr Tyr Ala Leu Val Asn
 1               5                  10                  15

Gln Trp Pro Gly Gly Phe Gln Ala Glu Val Thr Val Lys Asn Thr Gly
                20                  25                  30

Ser Ser Pro Ile Asn Gly Trp Thr Val Gln Trp Thr Leu Pro Ser Gly
            35                  40                  45
```

```
       Gln Ser Ile Thr Gln Leu Trp Asn Gly Asp Leu Ser Thr Ser Gly Ser
           50                  55                  60

Asn Val Thr Val Arg Asn Val Ser Trp Asn Gly Asn Val Pro Ala Gly
       65                  70                  75                  80

Gly Ser Thr Ser Phe Gly Phe Leu Gly Ser Gly Thr Gly Gln Leu Ser
                       85                  90                  95

Ser Ser Ile Thr Cys Ser Ala Ser
                       100

(2) INFORMATION FOR SEQ ID NO:4:

(i) SEQUENCE CHARACTERISTICS:
        (A) LENGTH: 106 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:4:

Thr Gly Ser Cys Lys Val Glu Tyr Asn Ala Ser Ser Trp Asn Thr Gly
       1               5                   10                  15

Phe Thr Ala Ser Val Arg Val Thr Asn Thr Gly Thr Thr Ala Leu Asn
                       20                  25                  30

Gly Trp Thr Leu Thr Phe Pro Phe Ala Asn Gly Gln Thr Val Gln Gln
                       35                  40                  45

Gly Trp Ser Ala Asp Trp Ser Gln Ser Gly Thr Thr Val Thr Ala Lys
           50                  55                  60

Asn Ala Ala Trp Asn Gly Ser Leu Ala Ala Gly Gln Thr Val Asp Ile
       65                  70                  75                  80

Gly Phe Asn Gly Ala His Asn Gly Thr Asn Asn Lys Pro Ala Ser Phe
                       85                  90                  95

Thr Leu Asn Gly Ala Thr Cys Thr Val Gly
                       100                 105

(2) INFORMATION FOR SEQ ID NO:5:

(i) SEQUENCE CHARACTERISTICS:
        (A) LENGTH: 103 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:5:

Ala Ala Ser Gly Gly Asn Cys Gln Tyr Val Val Thr Asn Gln Trp Asn
       1               5                   10                  15

Asn Gln Phe Thr Ala Val Ile Arg Val Arg Asn Asn Gly Ser Ser Ala
                       20                  25                  30

Ile Asn Arg Trp Ser Val Asn Trp Ser Tyr Ser Asp Gly Ser Arg Ile
                       35                  40                  45

Thr Asn Ser Trp Asn Ala Asn Val Thr Gly Asn Asn Pro Tyr Ala Ala
           50                  55                  60

Ser Ala Leu Gln Trp Asn Ala Asn Ile Gln Pro Gly Gln Thr Ala Glu
       65                  70                  75                  80

Phe Gly Phe Gln Gly Thr Lys Gly Ala Gly Ser Arg Gln Val Pro Ala
                       85                  90                  95

Val Thr Gly Ser Val Cys Gln
                       100
```

(2) INFORMATION FOR SEQ ID NO:6:

(i) SEQUENCE CHARACTERISTICS:
        (A) LENGTH: 104 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:6:

```
Gln Thr Ala Thr Cys Ser Tyr Asn Ile Thr Asn Glu Trp Asn Thr Gly
  1               5                  10                  15

Tyr Thr Gly Asp Ile Thr Ile Thr Asn Arg Gly Ser Ser Ala Ile Asn
             20                  25                  30

Gly Trp Ser Val Asn Trp Gln Tyr Ala Thr Asn Arg Leu Ser Ser Ser
         35                  40                  45

Trp Asn Ala Asn Val Ser Gly Ser Asn Pro Tyr Ser Ala Ser Asn Leu
     50                  55                  60

Ser Trp Asn Gly Asn Ile Gln Pro Gly Gln Ser Val Ser Phe Gly Phe
 65                  70                  75                  80

Gln Val Asn Lys Asn Gly Gly Ser Ala Glu Arg Pro Ser Val Gly Gly
                 85                  90                  95

Ser Ile Cys Ser Gly Ser Val Ala
                100
```

(2) INFORMATION FOR SEQ ID NO:7:

(i) SEQUENCE CHARACTERISTICS:
        (A) LENGTH: 97 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:7:

```
Val Ser Gly Ala Leu Lys Ala Glu Tyr Thr Ile Asn Asn Trp Gly Ser
  1               5                  10                  15

Gly Tyr Gln Val Leu Ile Lys Val Lys Asn Asp Ser Ala Ser Arg Val
             20                  25                  30

Asp Gly Trp Thr Leu Lys Ile Ser Lys Ser Glu Val Lys Ile Asp Ser
         35                  40                  45

Ser Trp Cys Val Asn Ile Ala Glu Glu Gly Gly Tyr Tyr Val Ile Thr
     50                  55                  60

Pro Met Ser Trp Asn Ser Ser Leu Glu Pro Ser Ala Ser Val Asp Phe
 65                  70                  75                  80

Gly Ile Gln Gly Ser Gly Ser Ile Gly Thr Ser Val Asn Ile Ser Val
                 85                  90                  95

Gln
```

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:8:

```
    Met Pro Arg Thr Thr Pro Ala
    1               5
```

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:9:

```
    Ala Gln Ala Ala Thr
    1               5
```

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
AGGAGGACAT CATGCCTAGG ACCACGCCCG CA                             32
```

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
GCCCAGGCCG CGACC                                                15
```

(2) INFORMATION FOR SEQ ID NO:12:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:12:

```
    Thr Met Ile Thr Asn Ser Ser Ser Pro Gly Asp Pro Arg
    1               5                   10
```

(2) INFORMATION FOR SEQ ID NO:13:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
AGGAAACAGC TATGACCATG ATTACGAATT CGAGCTCGCC CGGGGATCCT ACG        53
```

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:14:

Met Asp Pro Arg Thr
    1           5

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

TGGAGGAAAA AATTATGGAT CCTAGGACC                      29

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CGTCGGCGTG GGGGTGGGGG TCGG                            24

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

AATTTGGAAA AATTATG                                       17

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

ACCTTTTTAA TACCTAG                                       17

(2) INFORMATION FOR SEQ ID NO:19:

```
            (i) SEQUENCE CHARACTERISTICS:
                (A) LENGTH: 27 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:19:

ACCGCCGCGC AGGCGGCTCC CGGCTGC                                        27

(2) INFORMATION FOR SEQ ID NO:20:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:20:

ACCCCCACGC CGTAG                                                     15

(2) INFORMATION FOR SEQ ID NO:21:

(i) SEQUENCE CHARACTERISTICS:
                (A) LENGTH: 9 amino acids
                (B) TYPE: amino acid
                (C) STRANDEDNESS: Not Relevant
                (D) TOPOLOGY: linear (ii) MOLECULE TYPE: peptide (xi) SEQUENCE DESCRIPTION: SEQ ID NO:21:

Thr Ala Ala Gln Ala Ala Pro Gly Cys
            1               5
```